United States Patent
de la Mora Levy et al.

(10) Patent No.: US 8,287,535 B2
(45) Date of Patent: Oct. 16, 2012

(54) APPARATUS AND METHODS FOR INTERNAL SURGICAL PROCEDURES

(75) Inventors: Jose G. de la Mora Levy, Rochester, MN (US); Christopher J. Gostout, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1091 days.

(21) Appl. No.: 11/920,220

(22) PCT Filed: May 11, 2006

(86) PCT No.: PCT/US2006/018322
§ 371 (c)(1),
(2), (4) Date: Apr. 25, 2008

(87) PCT Pub. No.: WO2006/122279
PCT Pub. Date: Nov. 16, 2006

(65) Prior Publication Data
US 2009/0069806 A1   Mar. 12, 2009

Related U.S. Application Data

(60) Provisional application No. 60/679,760, filed on May 11, 2005.

(51) Int. Cl.
*A61B 18/18* (2006.01)
(52) U.S. Cl. ........................................................ 606/46
(58) Field of Classification Search .................. 604/22; 606/113–114, 41, 45, 46, 48, 49, 50
See application file for complete search history.

(56) References Cited

U.S. PATENT DOCUMENTS

| | | | | |
|---|---|---|---|---|
| 1,707,736 | A | * | 4/1929 | LaForce .................... 606/112 |
| 4,149,536 | A | * | 4/1979 | Villard ...................... 604/291 |
| 4,869,717 | A | * | 9/1989 | Adair ........................ 604/506 |
| 5,100,423 | A | * | 3/1992 | Fearnot ..................... 606/159 |
| 5,171,314 | A | * | 12/1992 | Dulebohn ................. 606/113 |
| 5,197,971 | A | * | 3/1993 | Bonutti ..................... 606/192 |
| 5,304,187 | A | * | 4/1994 | Green et al. .............. 606/151 |
| 5,336,227 | A | * | 8/1994 | Nakao et al. ............. 606/114 |
| 5,368,930 | A | | 11/1994 | Samples |
| 5,503,623 | A | * | 4/1996 | Tilton, Jr. .................. 604/13 |
| 5,509,900 | A | | 4/1996 | Kirkman |
| 5,509,923 | A | * | 4/1996 | Middleman et al. ..... 606/207 |
| 5,542,948 | A | | 8/1996 | Weaver et al. |

(Continued)

FOREIGN PATENT DOCUMENTS

JP       58131808 A    8/1983

(Continued)

OTHER PUBLICATIONS

Bernstein et al., "Standard biopsy forceps versus large-capacity forceps with and without needle," *Gastrointest. Endosc.*, Jun. 1995;41(6):573-576; available online Nov. 2, 2005: 6 pgs.

(Continued)

*Primary Examiner* — Manuel Mendez
(74) *Attorney, Agent, or Firm* — Mueting, Raasch & Gebhardt, P.A.

(57) ABSTRACT

Apparatus and methods for internal surgical procedures are disclosed. The apparatus and methods may involve supporting internal body locations, creating submucosal separations (blebs), and/or for resecting mucosal tissue separated from underlying tissue by a bleb.

9 Claims, 15 Drawing Sheets

U.S. PATENT DOCUMENTS

| | | | |
|---|---|---|---|
| 5,586,990 A * | 12/1996 | Hahnen et al. | 606/170 |
| 5,591,170 A * | 1/1997 | Spievack et al. | 606/82 |
| 6,021,524 A | 2/2000 | Wu et al. | |
| 6,080,474 A | 6/2000 | Oakley et al. | |
| 6,126,058 A * | 10/2000 | Adams et al. | 227/180.1 |
| 6,210,416 B1 | 4/2001 | Chu et al. | |
| 6,264,086 B1 | 7/2001 | McGuckin, Jr. | |
| 6,287,290 B1 * | 9/2001 | Perkins et al. | 604/516 |
| 6,371,963 B1 | 4/2002 | Nishtala et al. | |
| 6,398,798 B2 * | 6/2002 | Selmon et al. | 606/159 |
| 6,517,551 B1 * | 2/2003 | Driskill | 606/113 |
| 6,602,262 B2 * | 8/2003 | Griego et al. | 606/113 |
| 6,632,227 B2 | 10/2003 | Adams | |
| 6,743,228 B2 * | 6/2004 | Lee et al. | 606/47 |
| 6,770,071 B2 * | 8/2004 | Woloszko et al. | 606/41 |
| 7,156,837 B2 | 1/2007 | Ågerup | |
| 7,367,976 B2 * | 5/2008 | Lawes et al. | 606/51 |
| 2002/0161114 A1 | 10/2002 | Gunatillake et al. | |
| 2003/0009085 A1 | 1/2003 | Arai et al. | |
| 2003/0225460 A1 | 12/2003 | Gostout et al. | |

FOREIGN PATENT DOCUMENTS

| | | |
|---|---|---|
| JP | 63-92527 | 1/1990 |
| JP | 2000-210295 | 8/2000 |
| JP | 2002058674 A | 2/2002 |
| JP | 2002507449 A | 3/2002 |
| JP | 2002253557 A | 9/2002 |
| JP | 2003-52713 | 2/2003 |
| JP | 2003093395 A | 4/2003 |
| JP | 2003-153911 | 5/2003 |
| JP | 2003-534089 | 11/2003 |
| WO | WO 01/91646 A1 | 12/2001 |
| WO | WO 2006/122279 A2 | 11/2006 |

OTHER PUBLICATIONS

Carr-Locke et al., "Technology Assessment Status Evaluation: Bipolar and Multipolar Accessories, Feb. 1996," *Gastroenterol. Nursing*, 1998;21(4):187-189.

Conio et al., "Endoscopic Circumferential Esophageal Mucosectomy in a Porcine Model: An Assessment of Technical Feasibility, Safety, and Outcome," *Endosc.*, 2001;33(9):791-794.

de la Mora et al., "Intramural Endoscopic Dissection Using Pressurized Gas: A Novel Approach to Large Area Mucosal Resection and Polypectomy?" *Gastrointest. Endosc.*, Abstract 185, 2004;59(5):P91.

Forde et al., "Initial clinical experience with a bipolar snare for colon polypectomy," *Surg. Endosc.*, 1993;7:427-428.

Gilbert et al., "Status evaluation: hot biopsy forceps," *Gastrointest. Endosc.*, 1992;38(6):753-756.

Ginsberg, "Chapter 25, Accessories," *Colonoscopy: Principles and Practice*, Malden, MA, 2003:276-286.

Howell et al., "Successful Polyp Removal from Difficult to Visualize Areas of the Duodenum and Colon Using a Prototype Oblique Viewing Therapeutic Endoscope," *Gastrointest. Endosc.*, Abstract M1906, 2002;55(5):AB114.

Iishi et al., "Endoscopic resection of large pedunculated colorectal polyps using a detachable snare," *Gastrointest. Endosc.*, 1996;44(5):594-597.

Iishi et al., "Endoscopic Resection of Large Sessile Colorectal Polyps Using a Submucosal Saline Injection Technique," *Hepato-Gastroent.*, 1997;44:698-702.

Ishiguro et al., "Correlation of lifting verus non-lifting and microscopic depth of invasion in early colorectal cancer," *Gastrointest. Edosc.*, 1999;50(3):329-333.

Kajiyama et al., "Endoscopic resection of gastrointestinal submucosal lesions: a comparison between strip biopsy and aspiration lumpectomy," *Gastrointest. Endosc.*, 1996;44(4):404-410.

Kodama et al., "Treatment of superficial cancer of the esophagus: A summary of responses to a questionnaire on superficial cancer of the esophagus in Japan," *Surgery*, Apr. 1998;123(4):432-439.

McAfee et al., "Tiny snares prove safe and effective for removal of diminutive colorectal polyps," *Gastrointest. Endosc.*, 1994;40(6):301-303.

Nelson et al., "ASGE Technology Status Evaluation Report. Endoscopic Retrieval Devices," *Gastrointest. Endosc.*, 1999;50(6):932-934.

Peluso et al., "Follow-up of hot biopsy forceps treatment of diminutive colonic polyps," *Gasterointest. Endosc.*, 1991;37(6):604-606.

Rex, "Chapter 30, Missed Neoplasms and Optimal Colonoscopic Withdrawal Technique," *Colonoscopy, Principles and Practice*, Malden, MA, 2003:339-350.

Seitz et al., "Chapter 36, Difficult Polypectomy," *Colonoscopy, Principles and Practice*, Malden, MA, 2003:420-442.

Tappero et al., "Cold snare excision of small colorectal polyps," *Gastroenterol. Endosc.*, 1992;38(3):310-313.

Vanagunas et al., "Adequacy of "Hot Biopsy" for the Treatment of Diminutive Polyps: a Prospective Randomized Trial," *Am. J. Gastreoenterol.*, 1989;84(4):383-385.

Williams, "Chapter 29, Insertion Technique," *Colonoscopy, Principles and Practice*, Malden, MA, 2003:318-338.

Yamamoto et al., "A novel method of endoscopic mucosal resection using sodium hyaluronate," *Gastrointest. Endosc.*,, 1999;50(2):251-256.

Yang et al., "Prospective, randomized comparison of disposable and reusable forceps in gastrointestinal endoscopy," *Gastrointest. Endosc.*, 1994;40(6):671-674.

* cited by examiner

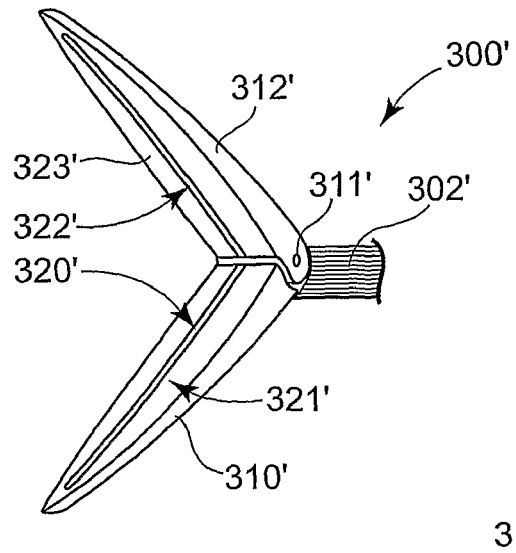
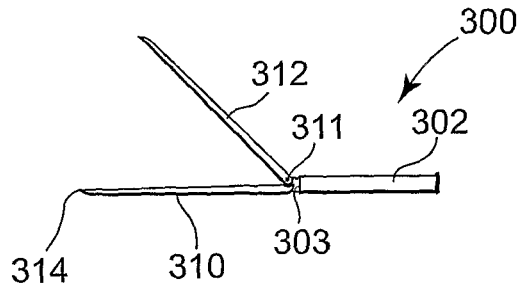
Fig. 24    Fig. 25
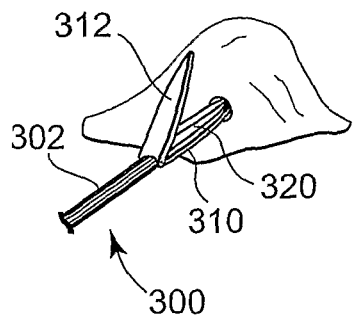
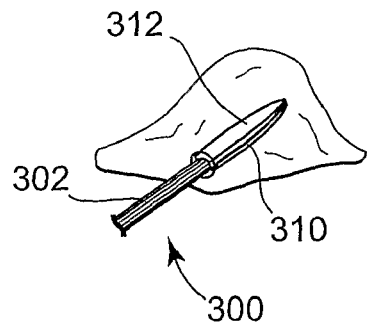
Fig. 26    Fig. 27
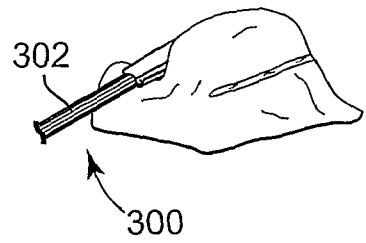
Fig. 28    Fig. 29

APPARATUS AND METHODS FOR INTERNAL SURGICAL PROCEDURES

RELATED APPLICATION

The present application is a U.S. National Stage Application of International Application No. PCT/US2006/018322, filed May 11, 2006 and titled APPARATUS AND METHODS FOR INTERNAL SURGICAL PROCEDURES, which claims the benefit under 35 U.S.C. §119(e) of U.S. Provisional Patent Application No. 60/679,760, filed May 11, 2005 and titled APPARATUS AND METHODS FOR INTERNAL SURGICAL PROCEDURES, all of which are hereby incorporated by reference in their entirety.

The present invention relates to internal surgical devices and methods. More particularly, the present invention relates to devices that may beneficially be used in conjunction with, e.g., mucosectomy procedures.

A variety of lesions such as superficial tumors, polyps, internal hemorrhoids, etc. may be difficult to remove from internal body locations because they have a relatively low profile with respect to surrounding tissue. The injection of liquids into the submucosa may be performed to facilitate surgical procedures such as, e.g., endoscopic mucosal resection (EMR), polypectomies in the gastrointestinal tract. The injected liquid may advantageously form a submucosal cushion beneath the tissue to be resected. Examples of liquids used to form the submucosal liquid cushion may include, e.g., saline solutions, sodium hyaluronate, glycerol solutions, methylcellulose solutions (such as those described in, e.g., U.S. Patent Application Publication No. 2003/0225460, titled COMPOSITIONS FOR GENERATING SUBMUCOSAL FLUID CUSHIONS, published Dec. 4, 2003), etc.

In the absence of a submucosal liquid cushion, it may be difficult for the practitioner to resect large sessile polyps and other lesions without injuring the underlying muscularis propria. By raising the lesion with a submucosal liquid cushion, the lesion may be isolated from the surrounding tissue and the underlying muscularis propria may be better protected from injury during resection of the lesion.

After the submucosal liquid cushion is formed, resection may be performed using a snare looped around the base of the submucosal liquid cushion. Examples of snare resection devices are described in, e.g., U.S. Pat. Nos. 5,542,948 (Weaver et al.) and 6,210,416 B1 (Chu et al.). Resection using the snare devices is typically augmented by electrosurgical energy to enhance cutting and, in some instances, to reduce bleeding.

SUMMARY OF THE INVENTION

The present invention provides apparatus and methods for internal surgical procedures. For example, the present invention may involve supporting internal body locations, creating submucosal separations (blebs), and/or for resecting mucosal tissue separated from underlying tissue by a bleb.

The apparatus, devices and methods of the present invention may find use in any suitable location within the body in which tissue is to be resected, including, e.g., the colon (to resect polyps or other tissue—with access through, e.g., the rectum), bladder (to resect bladder cancers—access through, e.g., the urethra), etc. In addition, the apparatus, devices and methods of the present invention may also be used to obtain deep muscle biopsies (to, e.g., diagnose neurologic disorders such as Parkinson's Disease, gastric motility disorders, etc.). In another potential application, the apparatus, devices and methods of the present invention may be used in transgastric surgical procedures in which instruments are delivered through an endoscope into the stomach. The instruments may then be advanced into the peritoneal cavity through, e.g., the stomach wall where selected surgical procedures could be performed. The apparatus, devices, and methods of the present invention may also be used for purposes not explicitly identified herein.

Among the internal surgical apparatus of the present invention, some apparatus that may be used to assist in tissue resection are depicted in FIGS. 55-57. The depicted apparatus may be used to prop open a variety of internal body locations, such as, e.g., body lumens (colon, gastrointestinal, blood vessels, urinary tract, etc.). In connection with blebs, the apparatus of FIGS. 55-57 may be used to maintain the submucosal space in the absence of, e.g., the gas, liquid, or other material used to create the submucosal space. Various other devices may potentially be advanced into the space defined by the cage, such as, e.g., imaging devices, tissue resection devices, etc.

The apparatus and methods for creating blebs may preferably involve the delivery of gas submucosally to separate tissue and create a gas-filled submucosal space. The gas may preferably be delivered at a pressure greater than atmospheric pressure. Using pressurized gas to create gas-filled blebs may provide a number of advantages over blebs formed using liquids. It has been observed that blebs created with pressurized gas may be higher, i.e., the gas-filled submucosal space may potentially be higher when measure normal to the plane of the underlying tissue. It has also been observed that tissue separation within the space of a gas-filled bleb may potentially be more pronounced than within a liquid-filled bleb.

Another potential advantage of a gas-filled bleb is that use of an electrosurgical cutting apparatus designed for "inside-out" resection may be more effective when used in connection with a gas-filled bleb. As described herein, some resection devices of the present invention may be effective when used to perform "inside-out" resection of tissue. Unlike conventional mucosal tissue resection in which a cutting instrument is used to cut tissue from the outside of a bleb towards the submucosal space within the bleb, methods of the present invention may preferably involve piercing the tissue of a bleb with a resection device and advancing at least a portion of the resection into the submucosal space. After the resection device (or a portion thereof) is located within the submucosal space, the tissue raised within the bleb can be cut from the inside of the submucosal space outwardly. By directing a cutting action outwardly from within the bleb, cutting and/or perforation of the tissue underlying the bleb may be much less likely to occur.

Among the gases that may be used to form gas-filled blebs, it may be preferred that the gas used be carbon dioxide. Potential advantages of carbon dioxide may potentially include, e.g., that carbon dioxide is readily absorbed by tissue and is unlikely to cause embolisms. In addition, carbon dioxide is not flammable and is readily available. More particularly, it may be preferred that the gas used consist essentially of carbon dioxide. It should be understood that small amounts of liquid, such as water, saline, etc., may be entrained within the carbon dioxide so long as the fluid delivered to form a gas-filled bleb is predominantly in the gas phase.

In still other embodiments of the present invention, it may be preferred to form a resection barrier of solid materials within the submucosal space of a bleb. By providing a solid resection barrier, conventional cutting instruments such as blades, etc. may be used to remove tissue with a significantly reduced risk of perforating the underlying tissue wall. The resection barrier may be made of a variety of materials including paraffin, curable materials (e.g., cyanoacrylate adhesives), foams, gels, etc. It may be preferred to use paraffin which can be heated to its liquid state and injected into the submucosal space of the bleb, where it cools and hardens to form a resection barrier.

In some embodiments, the resection apparatus may preferably include a resection frame located at the distal end of an elongated body. The resection frame preferably supports a cutting instrument that is capable of resecting tissue that extends through a resection opening defined by the resection frame. In some embodiments, the apparatus may preferably include staples and a stapling anvil such that retraction of the resection frame results in both resection of selected tissue and the placement of staples into the remaining tissue to close the edges surrounding the resected tissue.

The cutting instrument is preferably located between the two spaced-apart rails of the resection frame. When the resection frame is in an extended position with respect to the elongated body, the cutting instrument may preferably be displaced from the distal end of the elongated body. Movement of the resection frame to its extended position may be described as movement in the distal direction with respect to the elongated body. Movement of the resection frame to a retracted position preferably moves the cutting instrument towards the distal end of the elongated body or otherwise closes the resection opening. In some embodiments, such movement of the cutting instrument may be described as moving the cutting instrument in the proximal direction with respect to the elongated body.

When the resection frame is in the extended position, a resection opening may preferably be defined by the two spaced apart rails and the cutting instrument when the resection frame is in the extended position, wherein the size of the resection opening decreases and wherein tissue extending through the resection opening is severed by the cutting instrument when the resection frame is moved into the retracted position from the extended position.

It may be preferred that the resection frame include a pair of rails spaced apart from each other. The rails may preferably be rigid members that resist twisting and bending and that also exhibit significant strength in compression along their length as opposed to wires or cables used in snare-type resection devices that exhibit significant strength only in tension and provide only minimal resistance to bending and twisting.

The cutting instrument and the spaced apart rails may preferably define a U-shaped resection opening, wherein the U-shaped opening is preferably closed by the distal end of the elongated body. It may, for example, be preferred that the rails be straight and generally parallel to each other.

In some embodiments of the invention, the elongated body may include a fluid delivery lumen extending to the distal end of the elongated body, with a needle attached to the fluid delivery lumen at the distal end of the elongated body. It may be preferred that the needle be movable between an injection position in which the needle extends from the distal end of the elongated body and a sheathed position in which the needle is located within the elongated body.

An apparatus of the present invention that includes a fluid delivery lumen and needle may further preferably include a fluid source connected to the fluid delivery lumen. The fluid source may provide a fluid as needed to form submucosal fluid cushions in accordance with the preset invention. The fluid provided by the fluid source may be a liquid as is conventionally known. Alternatively, the fluid sources of the present invention may provide a gas to form the submucosal fluid cushion in accordance with the present invention. The gas may be, e.g., carbon dioxide.

The use of a resection frame as discussed in connection with the present invention may be advantageous in connection with a gas delivery system for forming blebs. For example, the resection frame may be extended and placed around the tissue to be resected. When in position, the resection frame can be used to apply pressure about the perimeter of the location at which a bleb is to be formed. The pressure provided by the resection frame may serve to restrict the size of the bleb by reducing the likelihood that the gas will separate tissue under the frame.

Other resection devices may also be provided in connection with the present invention. Those resection devices may be adapted for use in "inside-out" resection procedures as described herein. Some exemplary embodiments of such devices are described in connection with FIGS. 11-57 herein.

In one aspect, the present invention provides a tissue control device that includes a delivery sheath with a lumen that includes an opening at a distal end of the delivery sheath, wherein the delivery sheath defines a longitudinal axis extending between its distal end and a proximal end; and a cage located within the lumen of the delivery sheath, the cage having a plurality of struts extending from a proximal retainer to a distal retainer, wherein the cage is movable within the lumen such that the cage can be advanced distally out of the distal opening of the lumen. The cage has a restrained configuration when located within the lumen and an expanded configuration when advanced distally out of the lumen, wherein in the expanded configuration the struts move radially outward from the longitudinal axis.

In another aspect, the present invention provides a tissue control device for use in internal surgical procedures, the device including a delivery sheath having a lumen that comprises an opening at a distal end of the delivery sheath, wherein the delivery sheath defines a longitudinal axis extending between its distal end and a proximal end; and a cage located within the lumen of the delivery sheath, the cage including a plurality of struts extending in a distal direction from a proximal retainer, wherein the cage is movable within the lumen such that the cage can be advanced distally out of the distal opening of the lumen; wherein the cage has a restrained configuration when located within the lumen and an expanded configuration when advanced distally out of the lumen, wherein in the expanded configuration the struts move radially outward from the longitudinal axis.

In another aspect, the present invention provides methods of using the tissue control devices described in the preceding paragraphs by advancing the distal end of the delivery sheath to an internal body location before deploying the cage from the delivery sheath. The plurality of struts preferably move radially outward from the longitudinal axis as the cage is deployed.

In another aspect, the present invention provides an endoscopic resection apparatus including an elongated body with a proximal end and a distal end; a resection frame located proximate the distal end of the elongated body, the resection frame including two spaced apart rails, wherein the resection frame has an extended position and a retracted position; a cutting instrument located between the two spaced apart rails of the resection frame, wherein the cutting instrument is displaced from the distal end of the elongated body when the resection frame is in the extended position, and wherein movement of the resection frame to the retracted position moves the cutting instrument towards the distal end of the elongated body; and a resection opening defined by the two spaced apart rails and the cutting instrument when the resection frame is in the extended position, wherein the size of the resection opening decreases and wherein tissue extending through the resection opening is severed by the cutting instrument when the resection frame is moved into the retracted position from the extended position.

In another aspect, the present invention provides a method of separating mucosal tissue at a selected location by identifying a selected site in the mucosal tissue of a subject; locating a distal end of a gas delivery lumen submucosally at the selected site; delivering a gas into the mucosal tissue at the selected site through the distal end of the gas delivery lumen, wherein the gas is delivered at a gas pressure greater than the ambient atmospheric pressure, wherein the gas separates the mucosal tissue to create a gas-filled submucosal space.

In another aspect, the present invention provides a method of separating mucosal tissue at a selected location by delivering gas into mucosal tissue at a selected site, wherein the gas is delivered at a gas pressure greater than the ambient atmospheric pressure, and wherein the gas separates the mucosal tissue to create a gas-filled submucosal space; and forming a submucosal barrier in the submucosal space by injecting a barrier precursor into the gas-filled submucosal space, wherein the barrier precursor hardens in the submucosal space to form the submucosal barrier.

In another aspect, the present invention provides a method of resecting tissue at a selected location by identifying a selected site in the mucosal tissue of a subject; locating a distal end of a fluid delivery lumen submucosally at the selected site; delivering a fluid into the mucosal tissue at the selected site through the distal end of the fluid delivery lumen, wherein the fluid is delivered at a pressure greater than the ambient atmospheric pressure, and wherein a submucosal fluid cushion forms at the selected site; locating a resection device proximate the submucosal fluid cushion, wherein the resection frame is in the extended position, and wherein the submucosal fluid cushion extends through the resection opening; and moving the resection device into the retracted position, wherein the cutting instrument severs tissue raised above the submucosal fluid cushion.

In another aspect, the present invention provides a submucosal barrier kit including paraffin; a heating device adapted to heat the paraffin; and a delivery device adapted to deliver heated paraffin to a submucosal location.

In another aspect, the present invention provides a mucosal tissue separation kit including a pressurized gas source; and a sterile gas delivery device having a lumen, a tissue-piercing distal end, and a proximal end adapted to receive gas from the pressurized gas source, wherein the lumen extends from the proximal end of the gas delivery device to the distal end of the gas delivery device. Such kits may be supplemented by, e.g., a submucosal barrier precursor and a delivery device adapted to deliver the submucosal barrier precursor to a submucosal location. In other embodiments, the kit may be supplemented by, e.g., paraffin; a heating device adapted to heat the paraffin; and a delivery device adapted to deliver heated paraffin to a submucosal location.

In another aspect, the present invention provides a tissue resection device that includes an outer sheath with a distal end, and an outer sheath lumen opening at the distal end and an outer sheath proximal end; an inner sheath adapted to move within the outer sheath lumen, wherein the inner sheath includes a distal end and an inner sheath lumen opening at the distal end of the inner sheath; a core movable within the inner sheath lumen, wherein the core has a distal end; a first resection wire having a distal end attached to the distal end of the core and a proximal end attached to the inner sheath, wherein movement of the distal end of the core towards the distal end of the inner sheath causes a portion of the first resection wire to move radially away from the core; and electrical conductors operably connected to the resection wire, wherein electrical energy can be delivered from the proximal end of the outer sheath to the resection wire.

In another aspect, the present invention provides a tissue resection device that includes an elongated body with a distal end and a proximal end; a cutting head attached to the distal end of the elongated body, wherein the cutting head includes a cutting fin having a retracted position wherein the cutting fin is located within the body and an extended position wherein the cutting fin extends from the cutting head; wherein the cutting fin cuts tissue when drawing the elongated body and the cutting head in the proximal direction when the cutting fin is in the extended position.

In another aspect, the present invention provides a tissue resection device that includes an elongated body with a distal end and a proximal end; a hinged resection apparatus operably to the distal end of the elongated body, wherein the hinged resection apparatus includes first and second jaws, wherein at least one jaw of the first and second jaws is capable of rotating such that the first and second jaws have an open position in which tissue can be located between the first and second jaws and a closed position in which inner surfaces of the first and second jaws contact tissue located between the first and second jaws; at least one electrosurgical cutting member located on an inner surface of one or both of the first and second jaws, wherein tissue located between the first and second jaws can be cut by the cutting member; and wherein at least one of the first and second jaws includes a tissue piercing jaw, wherein the tissue piercing jaw is capable of piercing tissue when the tissue piercing jaw is advanced distally.

In another aspect, the present invention provides a tissue resection device that includes an elongated body having a distal end and a proximal end, wherein the distal end includes a first side and a second side located opposite from the first side; a pair of resection wires extending from the distal end of the elongated body, wherein each of the resection wires has a proximal end attached to the first side of the distal end of the elongated body, and wherein each of the resection wires has a distal end, wherein the distal ends of the resection wires are attached to each other proximate the second side of the distal end of the elongated body.

In another aspect, the present invention provides a tissue resection apparatus that includes a tubular body with a channel that opens at a distal end of the tubular body; a spreader sheath with a distal end and a proximal end, a longitudinal axis extending between the distal end and the proximal end of the sheath, wherein the spreader sheath is located within the channel of the tubular body and wherein the spreader sheath is axially movable distally and proximally within the channel of the tubular body; and first and second spreader arms proximate the distal end of the spreader sheath, the first spreader arm and the second spreader arm movable between a closed position in which the first spreader arm and the second spreader arm are aligned with the longitudinal axis and an open position in which the first spreader arm and the second spreader arm each form an angle of at least 15 degrees with the longitudinal axis; wherein the first spreader arm and the second spreader arm are in the closed position when the first spreader arm and the second spreader arm are located within the channel of the tubular body; and wherein the first spreader arm and the second spreader arm move into the open position as the first spreader arm and the second spreader arm are advanced distally out of the channel of the tubular body.

In another aspect, the present invention provides a tissue resection device that includes a sheath with a proximal end, a distal end, and a lumen that opens at the distal end of the sheath; and a snare located within the lumen, the snare being axially movable distally and proximally within the lumen, wherein the snare can be advanced distally out of the opening of the lumen; wherein the sheath has an angled tip proximate the distal end of the sheath, the angled tip including a section of the sheath that is oriented off-axis from a longitudinal axis defined by the sheath from its proximal end up to the section of the angled tip.

In another aspect, the present invention provides a tissue resection device that includes a sheath with a proximal end and a distal end; a lumen formed in the sheath, wherein the lumen includes a distal opening in a side of the sheath at a location proximal to the distal end of the sheath; and a snare located within the lumen, the snare being axially movable distally and proximally within the lumen, wherein the snare can be advanced distally out of the distal opening of the lumen.

In another aspect, the present invention provides a tissue resection device that includes a sheath with a proximal end, a distal end, and a lumen that includes an opening at the distal end of the sheath; a snare located within the lumen, the snare being axially movable distally and proximally within the lumen, wherein the snare can be advanced distally out of the opening of the lumen, wherein the snare includes a pair of wires terminating in a loop proximate the distal end of the sheath, and wherein the wires have rectangular cross-sectional profiles; and a plunger located proximate the proximal end of the sheath, wherein the plunger traverses the lumen in the sheath, and wherein the plunger is located between the pair of wires, the plunger including ribs cooperating with the wires, such that movement of the plunger transverse to a longitudinal axis of the sheath rotates the wires about their respective longitudinal axes, and wherein rotation of the wires causes the snare to curve off of the longitudinal axis of the sheath.

In another aspect, the present invention provides a method of providing a tissue resection barrier. The method includes inserting a barrier sheet into a submucosal space of a bleb and deploying the barrier sheet within the submucosal space, wherein the barrier sheet is located between submucosal tissue below the submucosal space and mucosal tissue above the submucosal space.

In another aspect, the present invention provides a barrier sheet deployment apparatus that includes a delivery sheath with a lumen that includes an opening at a distal end of the delivery sheath; and a barrier sheet located within the lumen of the delivery sheath, the barrier sheet having one or more coils while in the lumen.

These and other potential features and advantages of the present invention may be described below in connection with various exemplary embodiments of the invention.

BRIEF DESCRIPTIONS OF THE FIGURES

FIG. 24 is a perspective view of a portion of another exemplary resection device with jaws in the open position.

FIG. 25 is a side elevational view another exemplary resection device with one rotatable jaw in the open position.

FIGS. 26-29 are perspective views of one exemplary method of using the resection device of FIG. 25.

DESCRIPTION OF EXEMPLARY EMBODIMENTS OF THE INVENTION

In the following detailed description of some exemplary embodiments of the invention, reference is made to the accompanying figures which form a part hereof, and in which are shown, by way of illustration, specific embodiments in which the invention may be practiced. It is to be understood that other embodiments may be utilized and structural changes may be made without departing from the scope of the present invention.

The present invention may, in various embodiments, include three basic components, an injection apparatus capable of creating a submucosal fluid cushion, a resection apparatus capable of resecting tissue raised above the submucosal fluid cushion, and a stapling apparatus capable of stapling tissue as a part of the tissue removal process. It may be preferred that all three components, i.e., the injection apparatus, resection apparatus, and stapling apparatus be combined in the same instrument as depicted in many of the figures described below. It should, however, be understood that different components may be provided in separate instruments or that two of the components may be integrated into a single instrument. Furthermore, although the apparatus may preferably be adapted for endoscopic delivery, the apparatus of the invention may be introduced by any suitable technique, e.g., surgical, etc.

Figure 1:
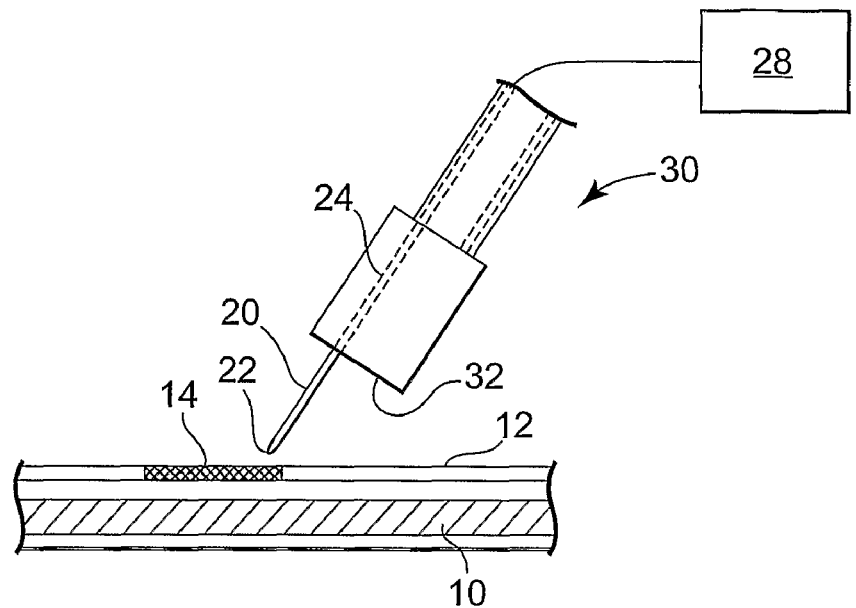
FIG. 1 is a cross-sectional view depicting initiation of submucosal fluid cushion formation in accordance with the present invention.

One exemplary apparatus according to the present invention is depicted in FIG. 1. The apparatus includes an elongated body 30 that has a distal end 32. The elongated body 30 may preferably be an endoscope with a suitable number of channels formed therein to accommodate the apparatus of the present invention.

The apparatus is depicted as positioned proximate a selected site 14 in tissue that includes mucosa 12 and underlying muscularis propria 10. The selected site 14 may preferably include a lesion in the form of a tumor, polyp, internal hemorrhoid, etc. that a practitioner would like to resect.

The depicted elongated body 30 includes a fluid delivery lumen 24 that extends through at least a portion of the elongated body 30. It may be preferred that the fluid delivery lumen 24 terminate proximate the distal end 32 of the elongated body 30. It may also be preferred that the fluid delivery lumen 24 extend proximally towards the proximal end (not shown) of the elongated body 30.

The apparatus depicted in FIG. 1 further includes a needle 20 that is preferably attached to the fluid delivery lumen 24 proximate the distal end 32 of the elongated body 30. The needle 20 may preferably be movable between an injection position in which the distal end 22 of the needle 20 extends from the distal end 32 of the elongated body 30 as seen in FIG. 1. It may also be preferred that the needle 20 be movable to a sheathed position in which the distal end 22 of the needle 20 does not extend past the distal end 32 of the elongated body 30, e.g., is retracted within the elongated body 30.

Figure 2:
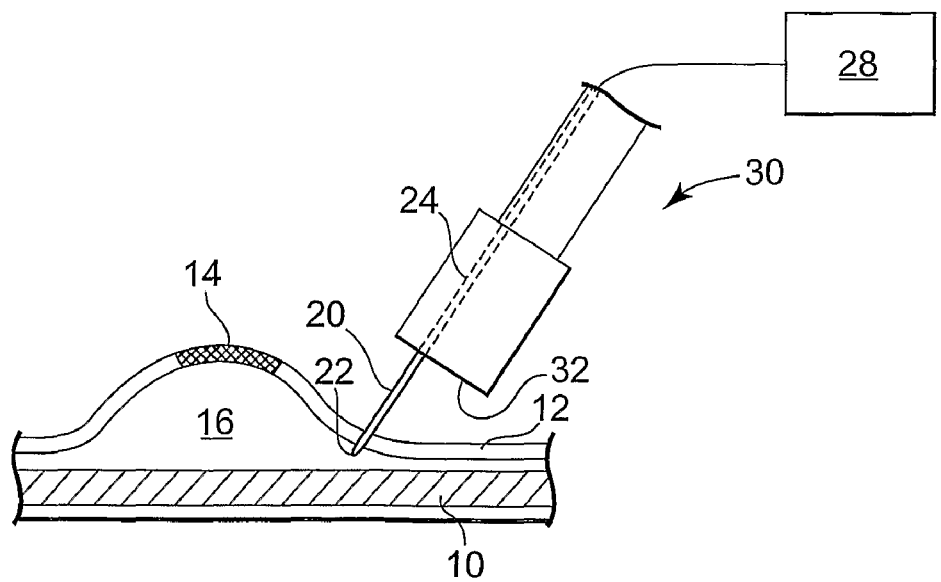
FIG. 2 is a partial cross-sectional view depicting formation of a submucosal fluid cushion in accordance with the present invention.

FIG. 2 depicts the apparatus of FIG. 1 after insertion of the distal end 22 of the needle 20 into the tissue proximate the selected site 14. It may be preferred that the needle 20 deliver a fluid into the tissue such that the mucosa 12 is separated from the underlying muscularis propria 10 by a submucosal fluid cushion 16. The fluid used to form the submucosal fluid cushion 16 is preferably delivered through the needle 20, which is preferably in fluid communication with a fluid source 28 through the fluid lumen 24 extending through the elongated body 30.

The fluid source 28 may take a variety of forms depending on the fluids being supplied. The fluid source 28 may be pressurized such that the fluid can be dispensed through a valve (and preferably pressure regulator) without the need for a separate pump. In other instances, a pumping mechanism may be provided in combination with a reservoir that may or may not be pressurized. The pressure at which the fluid is delivered may vary, although it may be preferred that the pressure for gases be 20 psig (140 kPa) or more. Pressure control may be provided by, e.g., a regulator or other pressure control device.

The fluid used to form the submucosal fluid cushion 16 may be liquid, gas, or combination thereof. In some instances, it may be preferred that the fluid used to form the submucosal fluid cushion 16 be a liquid, e.g., saline solutions, sodium hyaluronate, glycerol solutions, methylcellulose solutions (such as those described in, e.g., U.S. Patent Application Publication No. 2003/0225460, titled COMPOSITIONS FOR GENERATING SUBMUCOSAL FLUID CUSHIONS, published Dec. 4, 2003), etc.

In other instances it may be preferred that the fluid used to from the submucosal fluid cushion 16 be a gas, e.g., a gas including gaseous carbon dioxide. In other instances, it may be preferred that the fluid consist essentially of one or more gases, e.g., consist essentially of gaseous carbon dioxide. Using a gaseous fluid to form submucosal fluid cushions may have advantages over submucosal fluid cushions formed using liquid fluids as discussed herein.

The gases and/or liquids used to form submucosal spaces in blebs may, in some instances, preferably be replaced with solid (i.e., non-flowable) materials to form a resection barrier as discussed herein. Examples of some potentially suitable materials for resection barriers may be paraffin, biocompatible cyanoacrylate adhesive compositions, etc. In still other embodiments, the resection barrier may be provided by gel or polymer-based structural material (e.g., foam, etc.) that, as delivered, is uncured, but that can be expanded/cured within the submucosal space. In some embodiments, the resection barrier may preferably be biodegradable and/or bioresorbable such that it could slowly erode over time.

One potentially suitable expandable material may be a polylactic acid polymer (PLA, e.g., poly-DL-lactide, etc.) which may be provided as a liquid when dissolved in a solvent such as NMP (N-methyl-2-pyrrolidone), but hardens into a pliable structural material when the NMP diffuses out of the polymer mixture. Both NMP and the polymer PLA are generally considered to be inert and bioresorbable for use within the human (or animal) body. Other expandable structural materials may be known to those skilled in the art.

In those embodiments in which a fluid is used to create a bleb after which the fluid hardens, solidifies, cures or otherwise becomes non-flowable, the fluid may be referred to as a barrier precursor. In such methods, formation of the submucosal barrier may involve injecting a barrier precursor into the gas-filled submucosal space, wherein the barrier precursor hardens to form the submucosal barrier. Examples of some barrier precursors described herein may include, e.g., heated paraffin (heated, e.g., to a temperature of 65 degrees Centigrade or higher), cyanoacrylate compositions, uncured biocompatible foams, etc. Other barrier precursors may include, e.g., biocompatible photo-curable materials that can be cured upon the application of photo-radiation.

Figure 3:
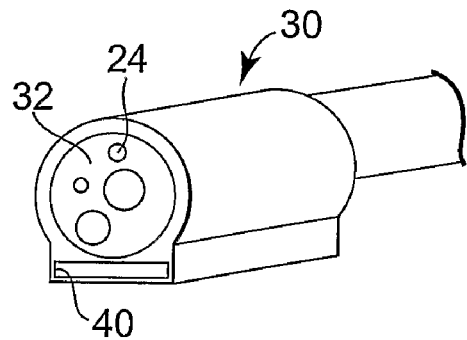
FIG. 3 is a perspective view of the distal end of one elongated body that may be used in connection with the present invention.

The apparatus according to the present invention may also preferably include resection devices to resect tissue raised by forming a submucosal fluid cushion. FIGS. 3-7 depict one exemplary embodiment of such a resection device and its operation. The resection device may preferably be provided within a housing located at the distal end 32 of the elongated body 30. As seen in FIG. 3, the housing may preferably include an opening 26 into which the needle 20 is retracted when in its sheathed position as discussed above with respect to FIGS. 1 & 2.

Figure 4:
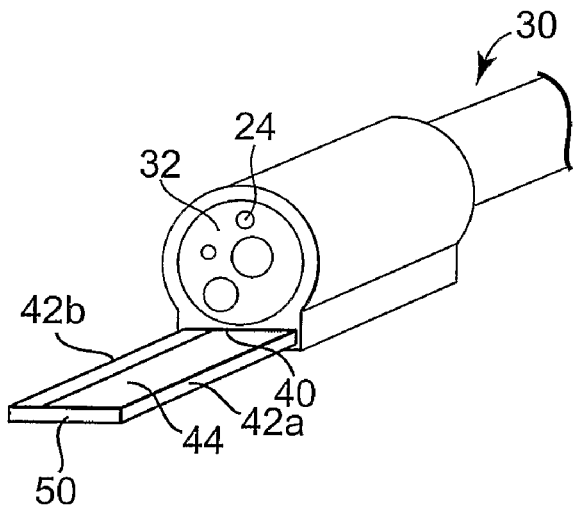
FIG. 4 is a perspective view of the elongated body of FIG. 3 with a resection frame in the extended position relative to the distal end of the elongated body.

The housing also preferably includes an opening 40 into which a resection frame retracts when in its retracted position. Turning to FIG. 4, a resection frame is depicted in an extended position in which the frame extends from the distal end 32 of the elongated body 30. The resection frame may preferably include two spaced apart rails 42a and 42b (referred to collectively as rails 42 herein) and a cross-member 50 connecting the two rails 42 at a location spaced from the distal end 32 of the elongated body 30.

Regardless of the exact construction of the resection frame, it may be preferred that the rails 42 and the cross-member 50 define a resection opening 44 located between the cross-member 50 and the distal end 32 of the elongated body 30. It may be preferred that the rails 42 and the cross-member 50 of the resection frame define a U-shaped resection opening 44.

It may further be preferred that the cross-member 50 include a cutting instrument such that movement of the resection frame to the retracted position (seen in FIG. 3) moves the cutting instrument on the cross-member 50 towards the distal end 32 of the elongated body 30. As the resection frame is moved from its extended position seen in FIG. 4 to its retracted position as seen in FIG. 3, the size of the resection opening 44 decreases.

Figure 5:
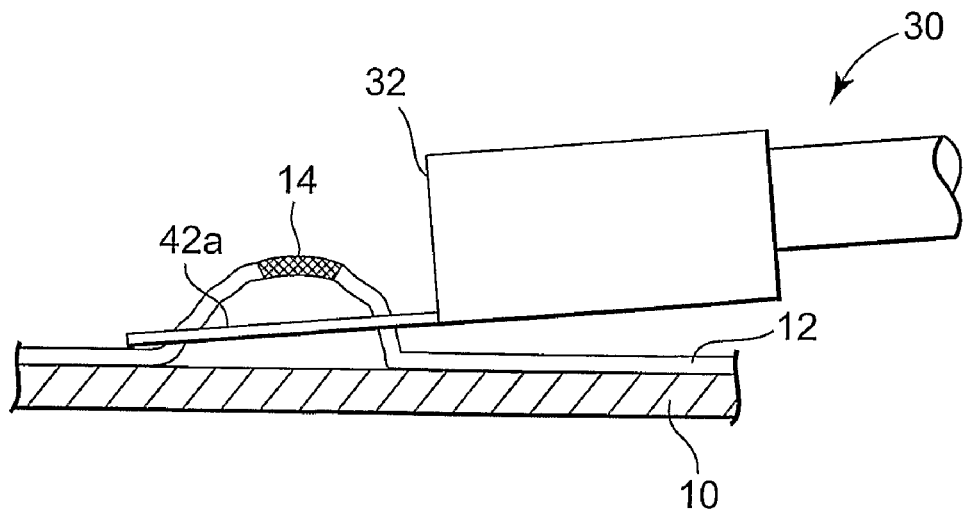
FIG. 5 is a partial cross-sectional view of the resection apparatus in position with a submucosal fluid cushion extending through the resection opening.
Figure 6:
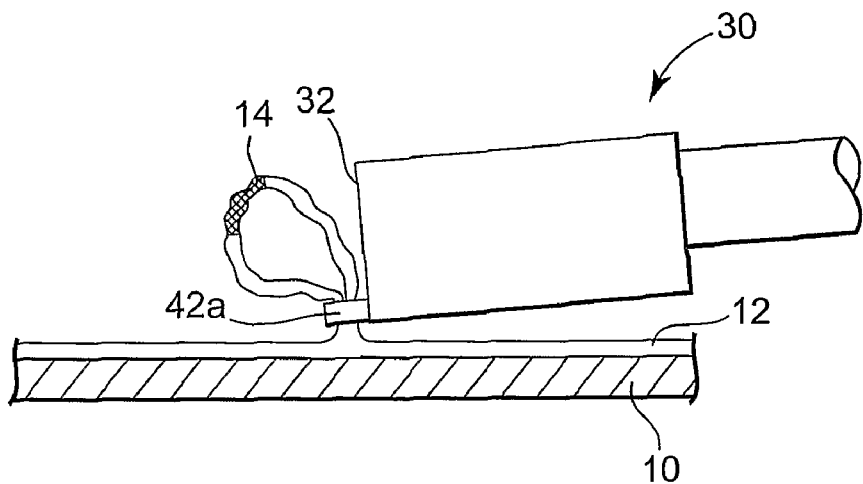
FIG. 6 is a partial cross-sectional view of the resection apparatus of FIG. 5 with the resection frame in the retracted position such that the tissue can be resected to remove the lesion located above the submucosal fluid cushion.

If selected tissue (such as tissue raised above a submucosal fluid cushion) extends through the resection opening 44 as depicted in FIG. 5, that tissue may be resected by the cutting instrument located on the cross-member 50 as seen in FIG. 6 where the resection frame is nearly completely retracted within the housing at the distal end 32 of the elongated body 30. It may be preferred that the selected tissue raised by the submucosal fluid cushion include a lesion 14 that is to be removed.

The cutting instrument on the cross-member 50 may take any suitable form, e.g., blade, wire, etc. The cutting action of any cutting instrument may be supplemented by, e.g., electrical energy (e.g., the cutting instrument may be an electrosurgical device).

It may be preferred that resection frames of the present invention be constructed with rails 42 that are rigid members. As used herein, a rigid member is a structure that resists twisting and bending and that also exhibits significant strength in compression along its length as compared to wires or cables used in snare-type resection devices (that exhibit significant strength only in tension and provide only minimal resistance to bending and twisting). It may further preferred that the rails 42 of resection frames of the present invention be straight and arranged generally parallel to each other.

Figure 7:
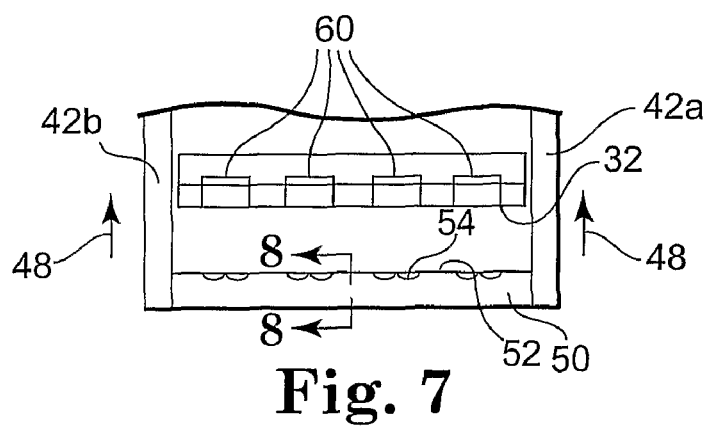
FIG. 7 depicts a stapling apparatus that may be used in connection with the present invention.
Figure 8:
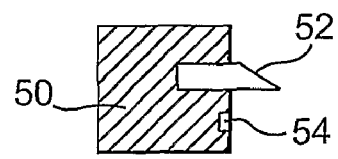
FIG. 8 is a cross-sectional view of a portion of the stapling apparatus taken along line 8-8 in FIG. 7.

FIGS. 7 & 8 depict a portion of the resection device to further describe an additional optional feature of the present invention. The resection frame including rails 42a and 42b and cross-member 50 are seen FIG. 7. The depicted cross-member 50 includes a blade 52 as a cutting instrument as seen in FIG. 8.

The cross-member 50 also preferably includes anvil surfaces 54 adapted to interact with staples 60 retained proximate the distal end 32 of the elongated body. The interaction between anvil surfaces 54 and the staples 60 preferably results in stapling of the tissue captured within the resection frame such that after removal of the tissue resected by the blade 52, the edges of the remaining tissue are held together by staples 60. The resection and stapling actions may preferably occur substantially at the same time as the resection frame is moved from its extended position towards its retracted position (in the direction of arrows 48 in FIG. 8). With the staples 60 and the stapling anvil 54 located on opposite sides of the resection opening when the resection frame is in the extended position, movement of the resection frame into the retracted position as discussed herein preferably forces the staples 60 into contact with the stapling anvil 54. The staples 60 and the stapling anvil 54 cooperate to staple tissue extending through the resection opening when the resection frame is moved into the retracted position from the extended position.

Although staples 60 are shown as being deformed by anvil surfaces 54, it will be understood that in some devices according to the present invention, the staples may be deformed by other mechanisms, e.g. the staples may be formed of shape memory materials (e.g. Nitinol, etc.) that deform in the absence of physical force.

Figure 9:
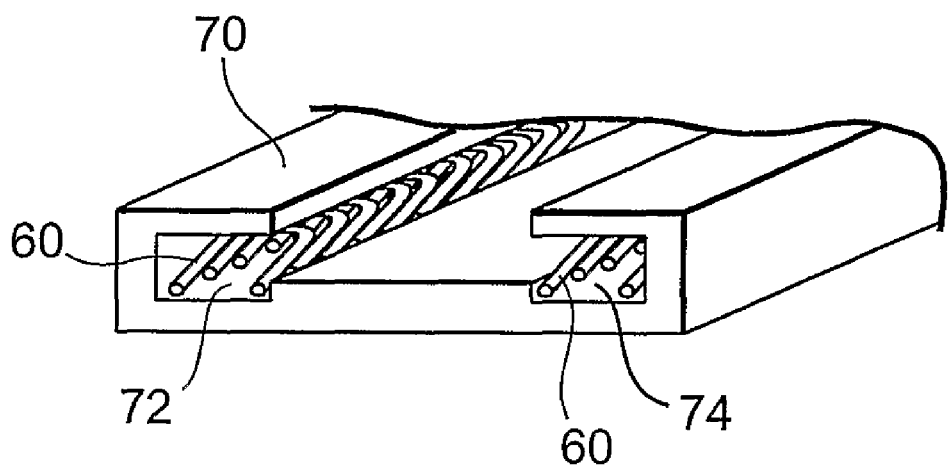
FIG. 9 is a perspective view of one exemplary staple cartridge that may be used in connection with the present invention.
Figure 10:
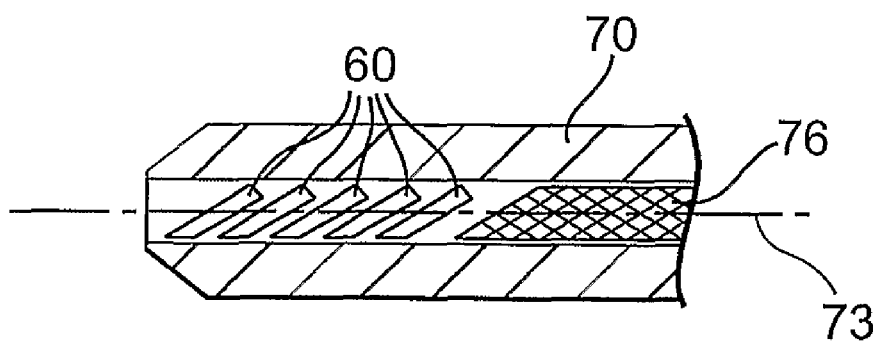
FIG. 10 is a cross-sectional view of a portion of the staple cartridge of FIG. 9.

FIGS. 9 & 10 depict another optional feature that may be incorporated into the apparatus of the present invention in the form of a staple cartridge capable of storing multiple sets of staples for delivery to multiple resection sites. The cartridge 70 includes staples 60 located in two channels 72 and 74. Although the cartridge 70 includes only two channels, it should be understood that cartridges according to the present invention may include more than two channels of staples.

The staples 60 may preferably be arranged within each of the channels 72 and 74 such that they are canted at an acute angle with respect to the longitudinal axis 73 of the channel (see FIG. 10). Each channel may also preferably include a member 76 adapted to bias the staples 60 towards the open end of the channel. The member 76 may be biased in the direction of the staples by a resilient member (e.g., spring, elastomeric article, etc.), hydraulic or pneumatic pressure, ratcheting mechanism, etc.). The member 76 may be used to advance the staples 60 toward the opening in the channel as staples 60 are dispensed from the cartridge 70.

FIGS. 11-16 depict another resection device that may be used in connection with the present invention. The resection device 100 may preferably be used in connection with an "inside-out" resection procedure as described herein.

The device 100 includes an outer sheath 102, an inner sheath 104 and an core 106. The inner sheath 104 and the outer sheath 102 are movable axially (i.e., along their lengths) with respect to each other with, e.g., the inner sheath 104 moving within a lumen of the outer sheath 102. The core 106 is axially movable with respect to the inner sheath 104 within a lumen in the inner sheath 104.

The device 100 also preferably includes one or more resection wires 108 provided to cut tissue. The depicted device includes two resection wires 108, although devices of the invention may include only one resection wire or three or more resection wires. The resection wires 108 are attached to the distal end 107 of the core 106. The proximal ends of the resection wires 108 are attached to the inner sheath 104, preferably proximate the distal end 105 of the inner sheath 104. Alternatively, the proximal ends of the resection wires 108 may be attached to the outer sheath 102 so long as the resection wires 108 do not significantly interfere with advancement of the outer sheath to a selected resection site.

The resection wires 108 may preferably cut tissue with the use of electrical energy delivered to the wires in accordance with known electrosurgical techniques. As such, it may be preferred that the device 100 include conductors that extend from the proximal end of the device (not shown) to the distal end (shown). The conductors may take the form of wires, electrical traces formed in or on the sheaths, etc.

Figure 11:
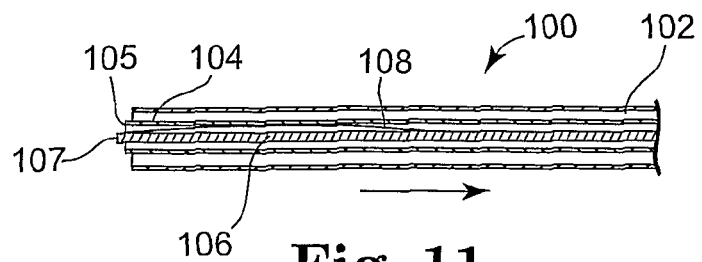
FIG. 11 is a partial cut-away side elevational view of one resection device according to the present invention.

As seen in FIG. 11, it may be preferred that the inner sheath 104, core 106 and resection wires 108 be retracted within the outer sheath 102 during advancement of the device 100 to a selected location. Once in position, the outer sheath 102 and inner sheath 104 are preferably manipulated such that the inner sheath 104 extends out of the outer sheath 102 (see, e.g., FIG. 12).

Figure 12:
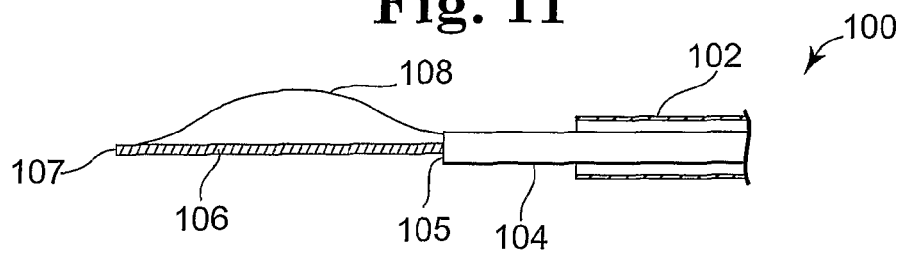
FIG. 12 is a side elevation of the device of FIG. 11 with the inner sheath and core extended.
Figure 13:
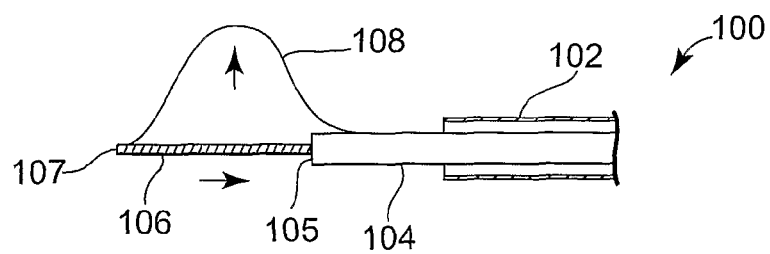
FIG. 13 is a side elevation of the device of FIGS. 11 & 12, with the core partially retracted.

When the core 106 is fully extended out of the inner sheath 104, the resection wires 108 are preferably in close proximity to the core 106. As, however, the distal end 105 of the core 104 and the distal end 107 of the core 106 are moved together, the resection wires 108 preferably move radially outward from the core 106 as seen in FIGS. 12 & 13 because their ends are fixedly attached to the inner sheath 104 and the core 106.

Figure 14:
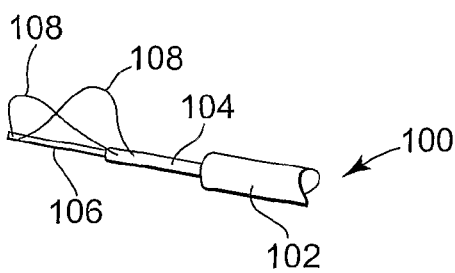
FIG. 14 is a perspective view of a device according to FIGS. 11-13, wherein the device includes two resection wires.
Figure 15:
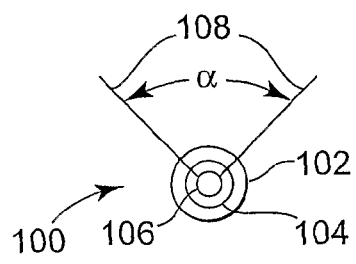
FIG. 15 is an axial view taken from the distal end proximally of the device of FIG. 14.

In the device 100 which includes two resection wires 108, it may be preferred that the wires 108 be offset circumferentially about the core 106, as is perhaps best seen in FIGS. 14 & 15. The offset between resection wires 108 may be measured in degrees and it may be preferred that the resection wires 108 be offset by an angle α (alpha) of about 30 degrees or more, 45 degrees or more, or even 90 degrees or more.

Figure 16:
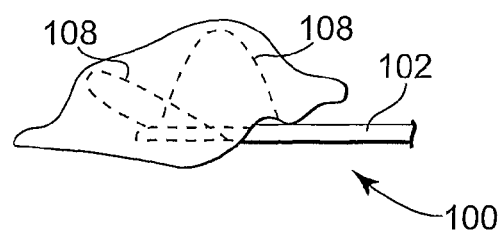
FIG. 16 is a perspective view of the device of FIGS. 14 & 15 within a bleb.

FIG. 16 depicts the device 100 deployed within the submucosal space of a bleb. The device 100 is preferably capable of piercing the tissue forming the bleb such that the core 106 with resection wires 108 can be deployed within the submucosal space. Once in position, the core 106 and inner sheath 104 are preferably manipulated such that the resection wires 108 extend radially outward from the core 106 to contact and cut the separated mucosal tissue. As discussed herein, it may be preferred that electrical energy be provided to the wires 108 to assist in the cutting.

In some embodiments, it may be preferred that the resection wires 108 be constructed of a shape memory metal (e.g., nickel titanium alloys, etc.) such that the shape of the resection wires 108 can be further modified based on the temperature of the wires 108. For example, if the wires 108 heat up during an electrosurgical procedure, that temperature increase can be advantageously used to provide additional height to the wires 108 or to cause the wires 108 to take on different selected shapes.

FIGS. 17-23 depict another resection device that may be used in connection with the present invention. The resection device 200 may also preferably be used in connection with an "inside-out" resection procedure as described herein.

Figure 17:
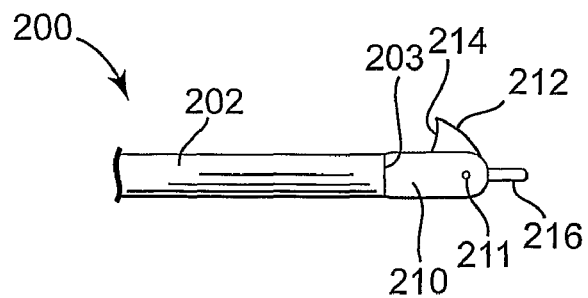
FIG. 17 is a side elevational view of a portion of another resection device according to the present invention.
Figure 18:
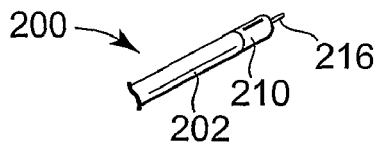
FIG. 18 is a perspective view of the resection device of FIG. 17 with the cutting member retracted.
Figure 19:
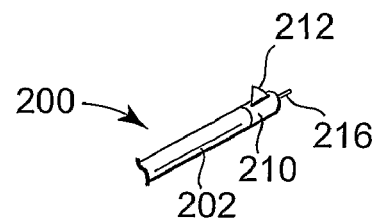
FIG. 19 is a perspective view of the resection device of FIG. 17 with the cutting member extended (as in FIG. 17).

The device 200 includes an elongated body 202 having a distal end 203. A cutting head 210 is attached to the distal end 203 of the elongated body 202. The cutting head 210 preferably includes a cutting member 212 that may preferably be in the form of a fin as seen in FIG. 17. The cutting member 212 preferably includes an edge 214 adapted to cut tissue. To assist in delivery and selective cutting of tissue, it may be preferred that the cutting member 212 be retractable such that the edge 214 can be withdrawn into the cutting head during, e.g., delivery of the device 200 to a selected location (see FIG. 18 which depicts device 200 with cutting member 212 retracted into cutting head 210). In the depicted embodiment, the cutting member 212 preferably rotates about pin 211 in cutting head 210.

The cutting member 212 may preferably be adapted for use as an electrosurgical cutting device in which electrical energy is provided to assist the cutting edge 214 in cutting tissue. It may be preferred that conductors be operably connected to the cutting member 212 to provide the electrical energy to the cutting member 212. The conductors preferably extend proximally along elongated body 202 to an electrical power source.

The cutting head 210 may also preferably include a puncture wire 216 or other piercing structure to assist the device 200 in piercing the tissue forming a bleb. The puncture wire 216 may preferably be a relatively thick monofilament polymer or other structure. The puncture wire 216 (or other structure) may preferably be retractable within the cutting head 210 to prevent unwanted piercing of tissue as the elongated body 202 is advanced to the selected location.

Figure 20:
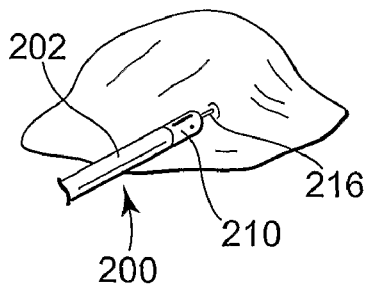
FIGS. 20-23 are perspective views of one exemplary method of using the resection device of FIG. 17.

FIGS. 20-23 depict use of the device 200 in connection with a bleb. In FIG. 20, the device 200 is advanced such that the puncture wire 216 pierces the tissue of the bleb. The cutting member 212 may preferably be in the retracted position within the cutting head 210 as seen in FIG. 20.

Figure 21:
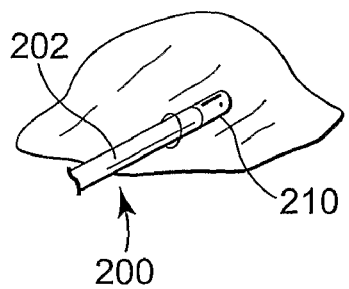

FIG. 21 depicts the device 200 after insertion into the bleb, with the cutting head 210 fully inserted into the submucosal space formed within the bleb. The puncture wire 216 is depicted as retracted back within the cutting head 210, although the puncture wire 216 may not necessarily have to be retracted at this point in the procedure.

Figure 22:
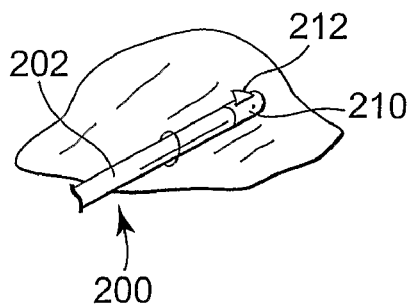
Figure 23:
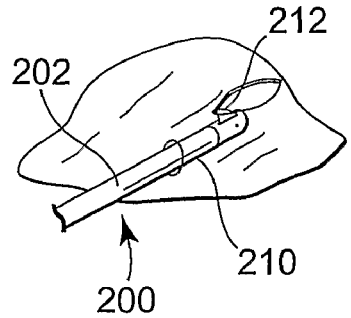
Figure 30:
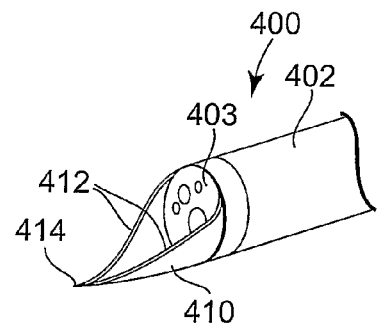
FIG. 30 is a perspective view of another exemplary embodiment of a resection device according to the present invention.

FIG. 22 depicts the device 200 in which the cutting member 212 has been extended from the cutting head 210. The cutting member 212 is also depicted as having initiated a cut into the tissue of the bleb. FIG. 23 depicts the cutting head 210 in the submucosal space after the elongated body 202 and attached cutting head 210 with cutting member 212 have been withdrawn in the proximal direction (i.e., moving out of the bleb through the opening formed during insertion) such that a portion of the tissue forming the bleb has been cut. After a desired amount of tissue has been cut, the cutting head 210 may be repositioned within the submucosal space for another cutting action.

FIGS. 24-29 depict another resection device that may be used in connection with the present invention. The resection device may also preferably be used in connection with an "inside-out" resection procedure as described herein.

FIG. 24 is a perspective view of one resection device 300' that includes an elongated body 302' with a cutting head at the distal end that includes jaws 310' and 312', both of which may preferably be hinged about an axis 311'. The jaw 310' preferably includes a cutting member 320' on the inner surface 321' and the jaw 312' preferably includes a cutting member 322' on its inner surface 323'. In some devices, it may be sufficient to provide a cutting member in only one of the jaws while the other jaw may provide, e.g., a surface against which the opposing jaw acts during the cutting. Furthermore, although the jaws 310' and 312' include cutting members 320' and 322' in the form of a single blade, it should be understood that the cutting member or members used in connection with the present invention may take any desired form or shape that provides the desired tissue resection.

The cutting members 320' and 322' may preferably employ electrical energy in an electrosurgical cutting action to assist with tissue resection as is known in the art. If electrical energy is used in the cutting, conductors may preferably be provided to deliver the required electrical energy to the cutting members. The electrical conductors may preferably extend along the elongated body from a proximal end (not shown) to the distal end.

One feature depicted in connection with resection device 300' is that both jaws 310' and 312' are hinged or otherwise capable of rotation with respect to the elongated body 302. In a variation on resection device 300', only one of the jaws may be hinged for rotation. One such embodiment is depicted in FIGS. 25-29. In that embodiment, the resection device 300 includes a jaw 310 that preferably does not rotate relative to the distal end 303 of elongated body 302. The opposing jaw 312 does, however, preferably rotate about axis 311 such that the jaws 310 and 312 can be moved from an open position (seen in FIG. 25) to a closed position (see in FIG. 27) in which the jaws are brought together to cut tissue located therebetween.

It may be preferred that one or both of the jaws 310 and 312 of device 300 have a shape or structure such that the jaw or jaws can pierce tissue, e.g., the tissue forming a bleb. In the depicted embodiment, jaw 310 preferably includes a tip 314 distal from the elongated body 302 that is preferably adapted to pierce tissue. In some instances, the tissue piercing may be assisted by electrosurgical energy and in other instances, the piercing may be a purely mechanical action.

FIG. 26 depicts device 300 in use in which the jaw 310 of device 300 is inserted into a bleb using the tissue piercing tip 314. The jaw 312 is preferably rotated away from jaw 310 such that the jaws are in the open position. As the device 300 is advanced distally, more of the jaw 310 is inserted into the submucosal space of the bleb.

FIG. 27 depicts the jaws 310 and 312 of the device 300 in the closed position such that tissue located between the inner surfaces of the jaws 310 and 312 can be cut. FIG. 28 depicts the bleb with an incision formed therein after removal of the device 300. FIG. 29 depicts the device 300 repositioned relative to the bleb to, e.g., cut the other side of the bleb to assist in removal of the tissue raised within the bleb.

FIGS. 30-33 depict another resection device that may be used in connection with the present invention. The device 400 includes an elongated body 402 and a cap 410 attached to the distal end 403 of the elongated body 402. The cap 410 may preferably be in the form of a scoop with two edges that include cutting members 412. The cutting members 412 may preferably include proximal ends attached to one side of the distal end 403 of the elongated body 402. The cutting members 412 also preferably include distal ends attached to the cap 410, wherein the distal ends converge at the tip 414 of the cap 410.

The cutting members 412 may preferably employ electrical energy in an electrosurgical cutting action to assist with tissue resection as is known in the art. If electrical energy is used in the cutting, conductors may preferably be provided to deliver the required electrical energy to the cutting members. The electrical conductors may preferably extend along the elongated body from a proximal end (not shown) to the distal end 403. It may be preferred that the cutting members 412 located on opposite sides of the cap 410 be electrically isolated from each other such that the cutting action of each cutting member 412 (if electrosurgically enhanced) can be independently controlled.

Figure 31:
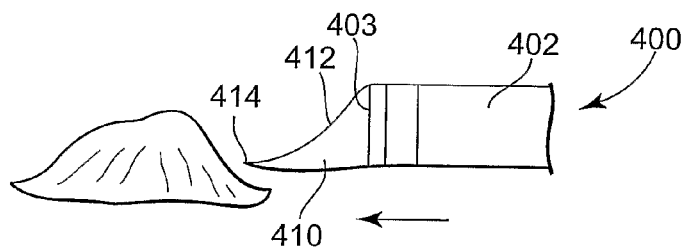
FIGS. 31-33 are side elevational views of one exemplary method of using the resection device of FIG. 30.
Figure 32:
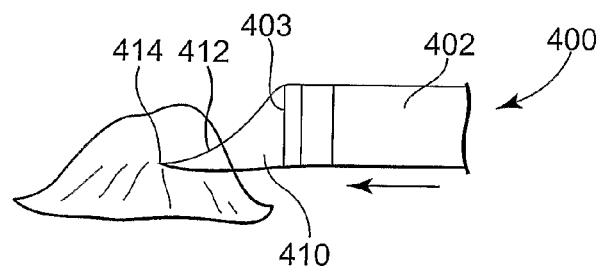
Figure 33:
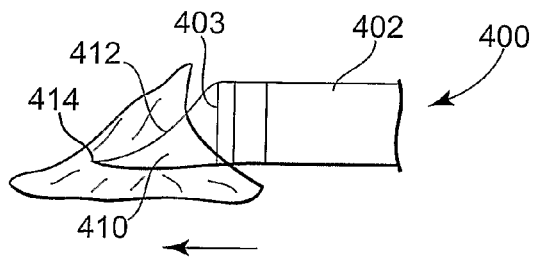

FIGS. 31-33 depict the device 400 in use resecting tissue raised within a bleb. The general scoop shape of the cap 410 may preferably assist in retaining the tissue in contact with the cutting members 412 attached to the cap 410 in a manner similar to a shovel. It may be preferred that the cap 410 include a relatively sharp tip 414 to assist in initial penetration and piercing of the tissue of the bleb.

A discussed herein, it may be beneficial to provide a resection barrier within the submucosal space of a bleb. Resection barriers may be used in connection with conventional resection devices and/or at least some of the resection devices of the present invention.

Figure 34:
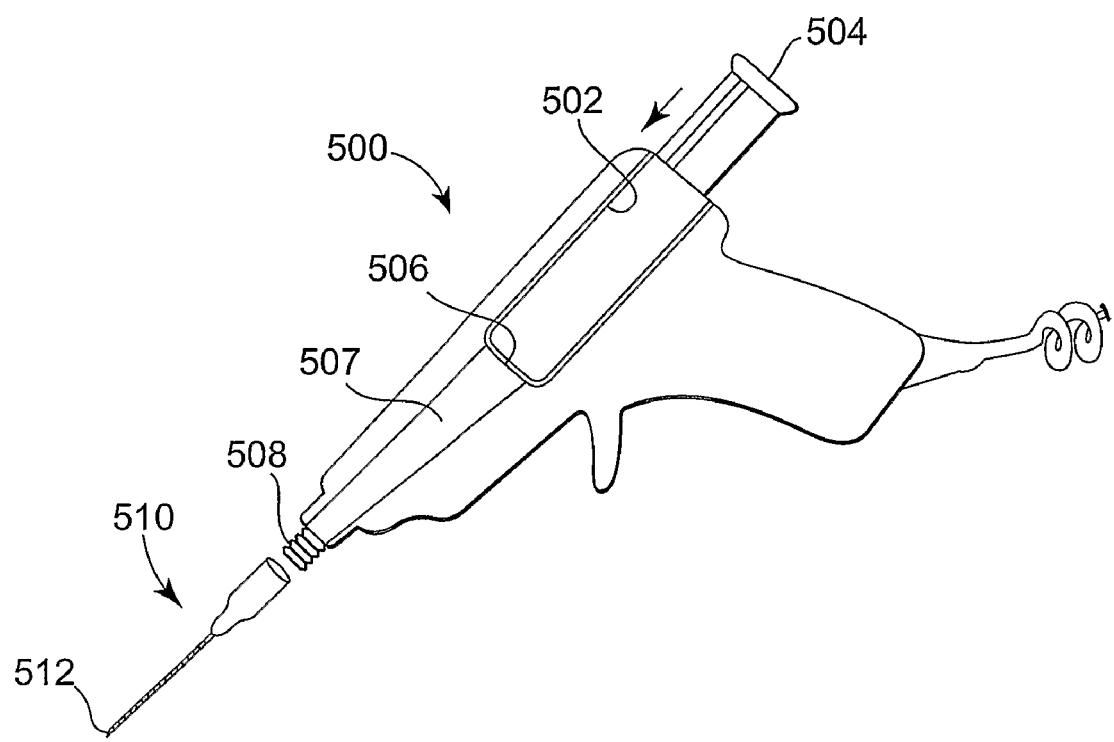
FIG. 34 is a cross-sectional view of one exemplary device for delivering heated paraffin into submucosal space according to the present invention.
Figure 35:
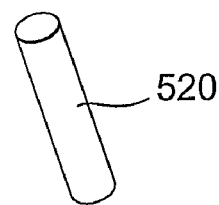
FIG. 35 is a perspective view of one stick of paraffin that may be used in connection with the device of FIG. 34.

In one exemplary embodiment, the resection barrier may be formed by injecting heated paraffin into the submucosal space of a bleb and allowing the paraffin to cool to a point at which it solidifies. FIG. 34 depicts one potential apparatus for delivering the heated paraffin to the submucosal space and FIG. 35 is a perspective view of one stick 520 of paraffin that may be used with the device of FIG. 34.

The paraffin used in connection with the present invention may preferably be sterile medical grade paraffin. Medical grade paraffin has a melting point at 65 degrees Celsius and cools/solidifies rapidly when placed in contact with tissue. In addition, it may be desirable to incorporate one or more agents into the paraffin to, e.g., decrease the melting point (such as an emulsifier), increase visibility (e.g., a colorant), etc.

The device 500 is in the general form of a conventional hot glue gun and may preferably include a heating chamber 502 and a plunger 504 adapted to force paraffin out of the heating chamber 502 through an orifice 506. The heated paraffin then preferably passes through a channel 507 to a port 508.

A delivery device 510 (preferably in the form of, e.g., a needle) is preferably attached to the port 508. The delivery device 510 preferably includes a lumen through which the heated paraffin travels to a distal end 512. It may be preferred that the distal end 512 of the delivery device be adapted to pierce tissue such as, e.g., the tissue of a bleb.

It may be preferred that the delivery device 510 include means for providing heat to the lumen such that the temperature of the heated paraffin passing through the lumen is maintained at a level that prevents solidification of the paraffin within the lumen (thus preventing delivery of the heated paraffin to the submucosal space). In some instances, the means for heating may be provided by electrical resistance heaters, fluid chambers adapted to receive heated fluid pumped to the delivery device, RF or microwave heat elements adapted to convert RF or microwave energy to thermal energy, etc. As an alternative to heating the lumen, the delivery device may preferably include sufficient insulation around the lumen such that the heated paraffin does not solidify during normal use of the device.

FIGS. 36-40 depict another apparatus that may be used to remove tissue. The tissue to be removed may or may not be raised using a submucosal cushion formed using gas, liquid, or solid material as described herein.

The apparatus 600 includes a tubular body 610 that includes a distal end 612 and a proximal end (not shown). In use, the distal end 612 is preferably advanced to the tissue to be resected while the proximal end preferably remains outside the body of the patient where it can be manipulated. The tubular body 610 may preferably be, e.g., an endoscope. The tubular body 610 preferably includes a channel in which a spreader sheath 620 is located. The spreader sheath 620 preferably includes a lumen in which a resection device 630 is located. The lumen extends along the length (longitudinal axis) of the sheath 620 and includes an opening at the distal end of the spreader sheath 620. The resection device 630 is axially movable distally and proximally within the lumen in the spreader sheath 620, such that the resection device 620 can be advanced distally out of the opening of the lumen of the spreader sheath 620.

Figure 36:
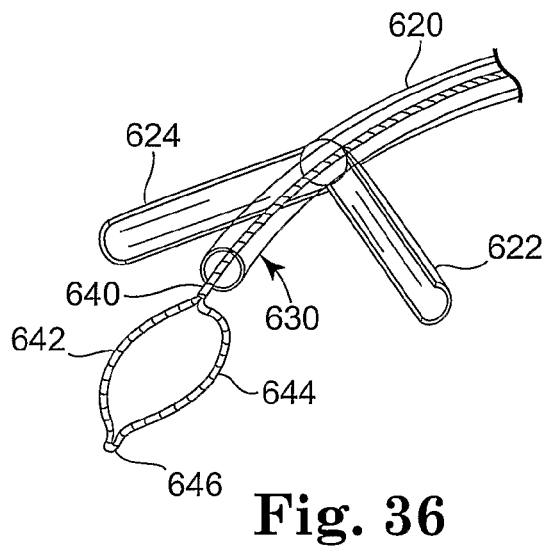
FIG. 36 is a perspective view of another resection apparatus according to the present invention.
Figure 38:
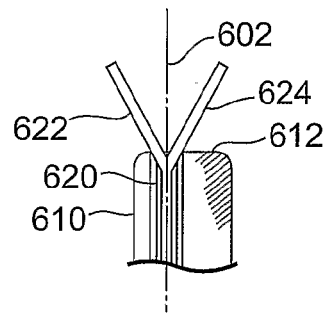
Figure 39:
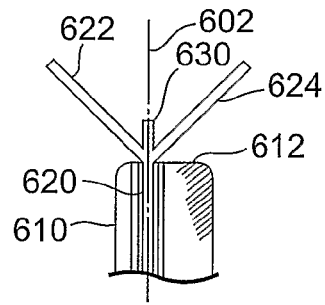

A perspective view of the spreader sheath 620 in its deployed configuration with a resection device in the form of a snare 640 advanced through its own sheath 630 is depicted in FIG. 36. FIGS. 37-40 depict the apparatus 600 in successive stages of deployment. Turning to FIG. 36, the spreader sheath 620 includes a distal end (shown) and a proximal end (not shown). The distal end of the spreader sheath 620 preferably includes spreader arms 622 and 624 movable between a closed position in which the spreader arms are aligned with the longitudinal axis 602 (see FIG. 37) and an open position (as depicted in, e.g., FIG. 40) in which the spreader arms 622 and 624 each form an angle β (beta) with the longitudinal axis 602. It may be preferred that the angle formed by each spreader arm 622 and 624 with the longitudinal axis 602 be at least 15 degrees, in some instances at least 30 degrees, and in other instances at least 45 degrees.

Figure 37:
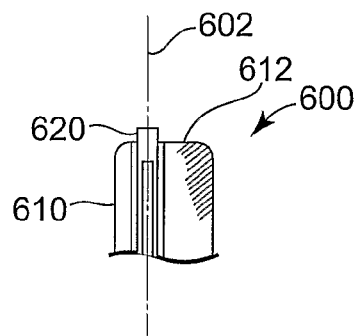
FIGS. 37-40 depict various stages in the deployment of the resection apparatus of FIG. 36.

The spreader arms 622 and 624 may be located in the closed position while within the channel of the tubular member 610 as depicted in, e.g., FIG. 37. It may be preferred that axial movement of the spreader sheath 620 along the longitudinal axis 602 in the distal direction out of the tubular member 610 allows the spreader arms 622 and 624 to assume the open configuration as depicted in the series of FIGS. 37-40. In the open configuration, it may be preferred, for example, that the spreader arms 622 & 624 have a length of about 1.5 centimeters while the spreader sheath 620 proximal of the spreader arms 622 and 624 have a size of 10 French. The spreader arms 622 & 624 may preferably open to an included angle of 90 degrees or more (with each spreader arm moving to a position of 45 degrees off of the longitudinal axis defined for the device).

It may be preferred that the spreader arms 622 and 624 are biased in the open configuration when not constrained within the channel of the tubular member 610. The biasing may be performed by a biasing means such as, e.g., elastic members, shape memory materials (e.g., nickel titanium alloys, polymers, etc.), mechanical springs (e.g., leaf, coil, etc.), pistons, etc. It may be preferred that the spreader as 622 and 624 move back into the closed position when the sheath 620 is withdrawn axially back within the tubular member 610 (in the proximal direction).

Although both spreader arms 622 and 624 are depicted as moving equally from the closed to the open position in FIGS. 36-40, it should be understood that the spreader arms 622 and 624 may not move equally in all embodiments. In some embodiments, for example, only one spreader arm may move from the closed to open position, with the other arm remaining stationary.

Also depicted in connection with the embodiment of FIGS. 36-40 is a resection device in the form of a snare 640 that is delivered through its own sheath 630. The snare 640 is, in the depicted embodiment, preferably advanced distally through a lumen in the spreader sheath 620 while in its own sheath 630. In use, the snare sheath 630 may be advanced out of the spreader sheath 620 as seen in, e.g., FIG. 39, followed by advancement of the snare 640 in the distal direction out of the snare sheath 630 as seen in, e.g., FIGS. 36 & 40. The snare 640 may preferably include two arms 642 and 644 that are connected at the distal end 646 of the snare 640. If desired, the snare 640 may perform tissue resection with the aid of electrosurgical energy.

Figure 41:
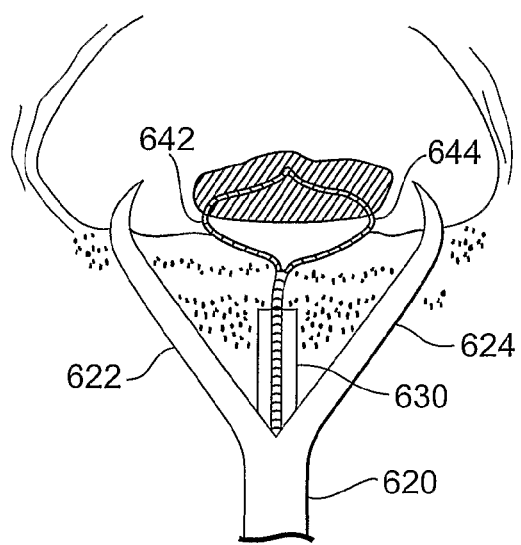
FIG. 41 depicts one method of use of the resection apparatus of FIG. 36.
Figure 40:
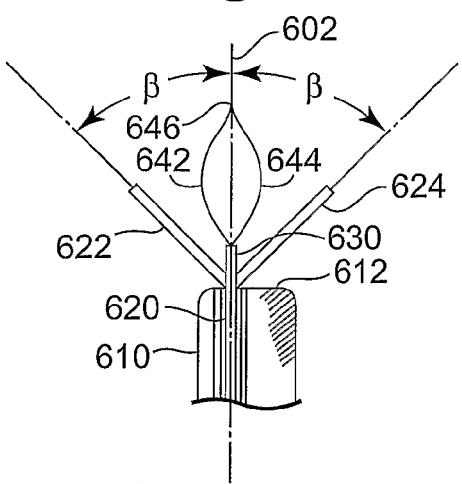

One potential use for the apparatus of FIGS. 36-40 is in a polypectomy in which the polyp is located, e.g., just above or beyond a haustral fold in the colon. One such situation is depicted in FIG. 41. Although some techniques using existing resection devices have been used to resect such tissue, some polyps nevertheless remain difficult to remove. When using the apparatus of FIGS. 36-40, however, the spreader arms 622 & 624 may be used to push a haustral fold down and keep it in that position, clearing the view to the polyp and allowing the snare 640 to more easily encircle the polyp. The apparatus of FIGS. 36-40 could also be used to hold haustral folds down to explore their backsides to determine whether additional polyps might be located there.

FIGS. 42-46 depict another resection device that may be used to remove tissue. The tissue to be removed may or may not be raised using a submucosal cushion formed using gas, liquid, or solid material as described herein.

Figure 42:
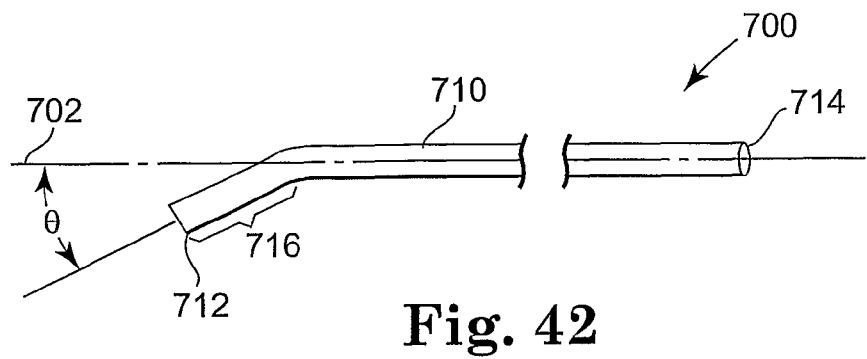
FIGS. 42 & 43 depict another resection device with an angled tip.

As depicted in FIG. 42, the resection device 700 may include a sheath 710 having both a distal end 712 and a proximal end 714. The sheath 710 preferably includes a lumen that opens at the distal end 712.

The device 700 also preferably includes a snare 720 located within the lumen of the sheath 710. The snare 720 is preferably axially movable distally and proximally within the lumen of the sheath 710, such that the snare 720 can be advanced distally out of the opening of the lumen at the distal end 712 of the sheath 710.

The sheath 710 preferably includes an angled tip proximate the distal end 712 of the sheath 710. The angled tip includes a section 716 of the sheath 710 that is oriented off-axis from a longitudinal axis 702 defined by the sheath 710 from the proximal end 714 up to the section that includes the angled tip. The section 716 of the sheath 710 that includes the angled tip may preferably include 10% or less of the total length of the sheath 710 from the proximal end 714 to the distal end 712.

Figure 43:
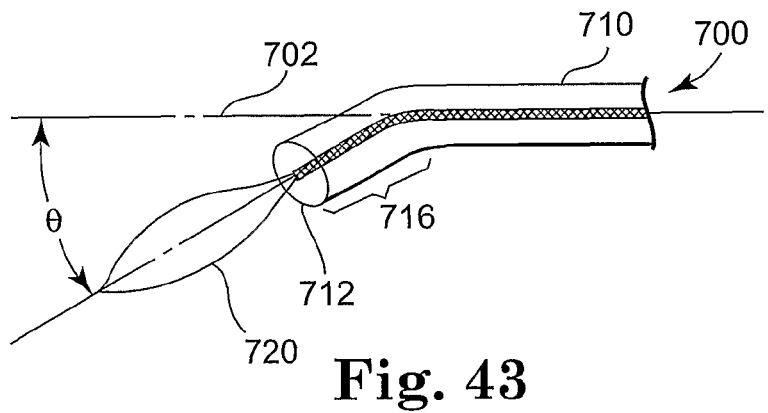

As a result of the angled tip, it may be preferred that the snare 720, when advanced distally out of the distal end 712 of the sheath 710, exit the sheath 710 at an angle θ (theta) that may preferably be 20 degrees or more off of the longitudinal axis 702 (as depicted in FIG. 43). Although the section 716 of the sheath forming the angled tip is depicted as being generally straight along its length, it should be understood that it could be curved or constructed of multiple sections that are straight and/or curved. Regardless, it is preferred that the snare 720 exit the sheath 710 at an angle off of the longitudinal axis 702 as discussed herein.

Figure 44:
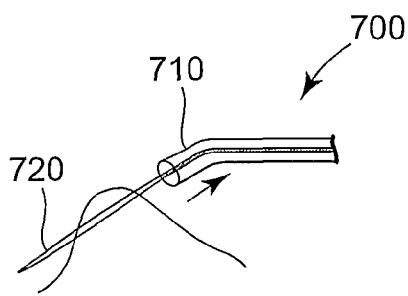
FIGS. 44-46 depict one method of using the resection device of FIGS. 42 & 43.
Figure 45:
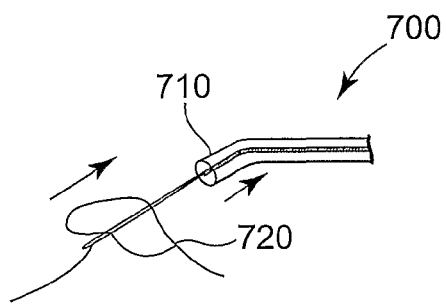
Figure 46:
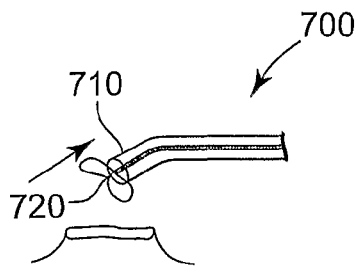

Potential advantages of the angled tip may include, e.g., enhanced stiffness in the snare 720 as it exits the sheath 710 as compared to a conventional sheath in which the snare exits the sheath along the longitudinal axis of both components (i.e., the sheath and the snare). This additional stiffness in the snare may improve the ability of the snare to encircle polyps or other tissues as depicted in the series of FIGS. 44-46.

Figure 47:
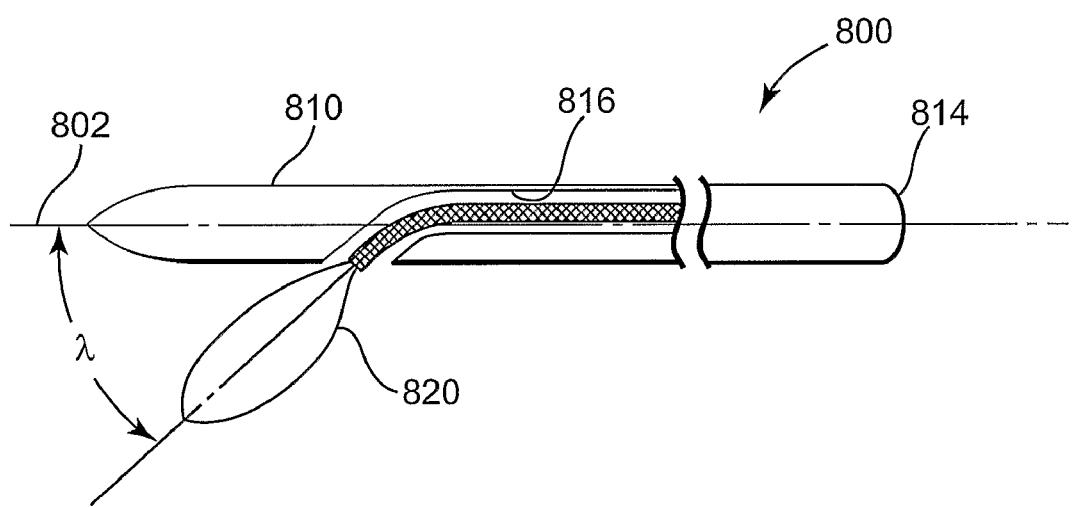
FIG. 47 depicts another resection device.

Another embodiment of a resection device that may be used to remove tissue is depicted in FIG. 47. The tissue to be removed may be raised from the surrounding tissue (as in the case, e.g., of a polyp). In some instances, the tissue may or may not be raised using a submucosal cushion formed using gas, liquid, or solid material as described herein.

The resection device 800 may include a sheath 810 having both a distal end 812 and a proximal end 814. The sheath 810 preferably includes a lumen 816 that opens through the side of the sheath 810 at a location proximal from the distal end 812 of the sheath 810. The sheath 810 itself, however, preferably extends along the longitudinal axis 802 defined between its distal and proximal ends 812 and 814. In contrast, a distal section of the lumen 816 proximate the distal side opening is oriented off-axis from the longitudinal axis defined between the proximal and distal ends 812 and 814 of the sheath 810. It may be preferred that the side opening in the lumen be located within the distal-most 10% or less of the total length of the sheath 810 (as measured between its proximal and distal ends 812 & 814).

The device 800 also preferably includes a snare 820 located within the lumen 816 of the sheath 810. The snare 820 is preferably axially movable distally and proximally within the lumen 816 such that the snare 820 can be advanced distally out of the opening of the lumen 816 through the opening in the side of the sheath 810.

Because the snare 820 exits the sheath 810 through its side, the snare 820 preferably forms an angle λ (lambda) with the longitudinal axis 802 that may preferably be 20 degrees or more off of the longitudinal axis 802. Potential advantages of the angled snare 820 may include, e.g., enhanced stiffness in the snare 820 as it exits the sheath 810 as compared to a conventional sheath in which the snare exits the sheath along the longitudinal axis of both components (i.e., the sheath and the snare). This additional stiffness in the snare 820 may improve the ability of the snare to encircle polyps or other tissues.

Figures 48A, 48B:
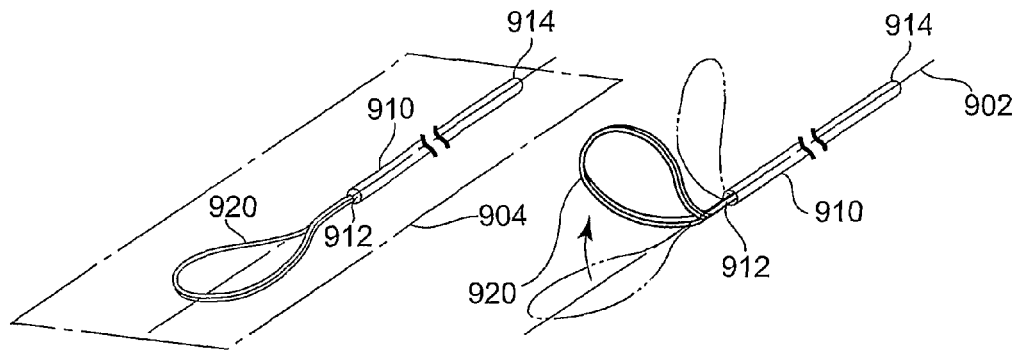
FIGS. 48A-48C depict another resection device in various configurations.
Figure 48C:
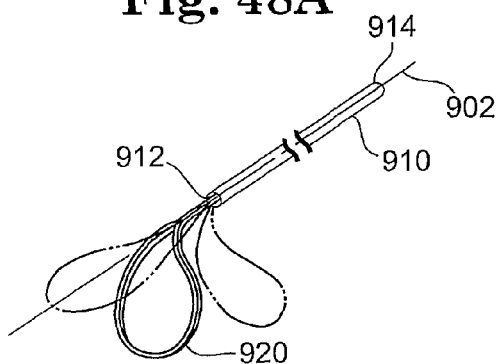

Still another embodiment of a resection device is depicted in FIGS. 48A-48C, 49A-49C, and 50A-50C. Turning to FIGS. 48A-48C, the resection device 900 is in the form of a sheath 910 that includes a lumen in which a snare 920 is located. The sheath 910 includes both a distal end 912 and a proximal end 914. The lumen in the sheath 910 preferably opens at the distal end 912 of the sheath.

The snare 920 is preferably axially movable distally and proximally within the lumen of the sheath 910, such that the snare 920 can be advanced distally out of the opening of the lumen at the distal end 912 of the sheath 910. It may be preferred that the snare 920 be movable from orientations in which the snare 920 lies substantially within a plane 904 in which the longitudinal axis defined by the distal end 912 and proximal end 914 of the sheath 910 lies as seen in FIG. 48A. Manipulation of the snare as described herein can, however, cause the snare 920 to curve above or below the plane 904. For example, FIG. 48B depicts the snare 920 curving away from the plane 904 in one direction while FIG. 48C depicts the snare 920 curving away from the plane 904 in the opposite direction.

Figure 49A:
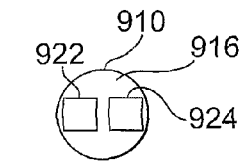
FIGS. 49A-49C depict cross-sectional views of the wires leading to the snare in the device of FIGS. 48A-48C.
Figure 49B:
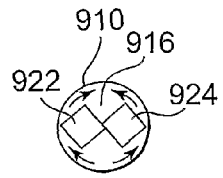
Figure 49C:
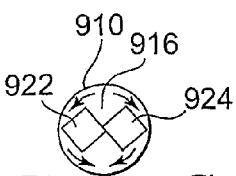

Movement of the snare 920 between the positions depicted in FIGS. 48A-48C may be effected by manipulating the wires 922 and 924 of the snare within the lumen 916 of the sheath 910. FIGS. 49A-49C depict the orientation of the wires 922 and 924 within the lumen 916 at a position between the distal end 912 and the proximal end 914 of the sheath 910. As seen in FIG. 49A, the wires 922 and 924 are in a neutral orientation within the lumen 916. In FIG. 49B, the wire 922 is rotated clockwise about its axis while wire 924 is rotated counterclockwise. The result is depicted in FIG. 48B in which the snare 920 curves upward from the plane 904. In FIG. 49C the wires 922 and 924 are rotated in the opposite direction, i.e., wire 922 is rotated counterclockwise from the neutral position of FIG. 49A and wire 924 is rotated clockwise. The result is depicted in FIG. 48C in which the snare 920 curves downward with respect to the plane 904.

Figure 50A:
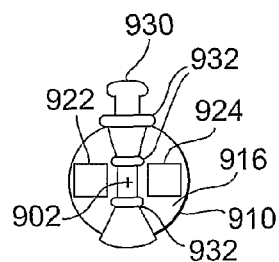
FIGS. 50A-50C depict one mechanism that may be used to manipulate the wires in the resection device of FIGS. 48A-48C.
Figure 50B:
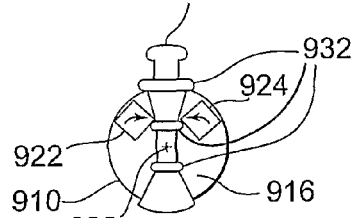
Figure 50C:
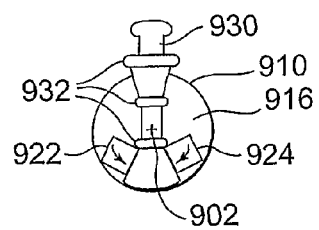

FIGS. 50A-50C depict one apparatus that may be used to rotate the wires 922 and 924 as discussed herein to control the orientation of the snare 920. The apparatus includes a plunger 930 that may preferably be located proximate the proximal end 914 of the sheath 910. The depicted plunger 930 traverses the lumen 916 of the sheath 910 and is located between the wires 922 and 924. The plunger 930 may preferably include ribs 932 that cooperate with the wires 922 and 924 such that movement of the plunger 930 transverse to the longitudinal axis 902 (out of the page in FIGS. 50A-50C) rotates the wires 922 and 924 about their respective longitudinal axes.

Although FIGS. 50A-50C depict one mechanism for rotating the wires 922 and 924, many other mechanisms that accomplish the same function may be used in place of that depicted in FIGS. 50A-50C.

Figure 51:
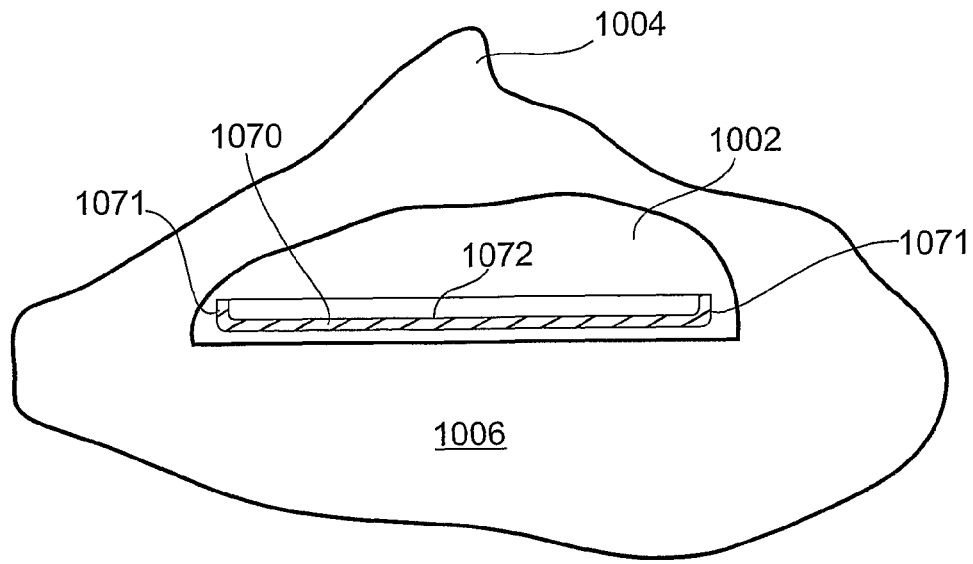
FIG. 51 is a cross-sectional view of a bleb with a barrier sheet located therein.

FIGS. 51-54 depict another exemplary apparatus and method of the present invention in which a barrier sheet is deployed within the submucosal space of a bleb. FIG. 51 in particular depicts (in partial cross-sectional view) a barrier sheet 1070 located within the submucosal space 1002 that may preferably be located beneath, e.g., a polyp 1004 or other tissue to be resected. The barrier sheet 1070 may preferably include a central area 1072 and a raised lip 1071 that may preferably extend about a periphery of the central area 1072. The lip 1071 may be integrally formed with the material of the central area 1072 or it may be attached thereto. Furthermore, the lip 1071 may extend continuously about the perimeter of the central area 1072 or it may be discontinuous.

The barrier sheet 1070 is provided to act as a barrier to protect the underlying submucosal tissue during resection procedures. It may be preferred that conventional cutting instruments such as blades, etc. that may be used to remove tissue cannot readily perforate or cut the barrier sheet 1070. As a result, the barrier sheet 1070 may preferably significantly reduce the risk of perforating an underlying tissue wall. Other potential functions of the barrier sheet 1070 may include, e.g., reducing diffusion of any gas, liquid, foam, etc. introduced into the tissue underlying the barrier sheet, providing a tactile response to the practitioner during resection (thus providing, e.g., an indication of the location of the bottom of the submucosal space or the edges of the space—using, e.g., the optional lip 1071), etc.

In some instances, it may be preferred that the barrier sheets of the present invention be manufactured of one or more materials that exhibit shape memory properties. For example, it may be preferred that the lip 1071 of the barrier sheet 1070 be manufactured of shape memory materials while the central area 1072 may be manufactured of materials that may or may not exhibit shape memory properties. Alternatively, the central area 1072 may be manufactured of shape memory materials while the lip 1071 is manufactured of materials that may or may not exhibit shape memory properties. Barrier sheets manufactured of two or more different materials may be manufactured by a variety of techniques, e.g., coextrusion, coinjection molding, insert molding, etc.

Delivery of the barrier sheet 1070 into the submucosal space 1002 may be accomplished by any suitable technique. One exemplary apparatus and technique may be described in connection with FIGS. 52-54. Generally, it may be preferred to deliver the barrier sheet 1070 using a catheter-like device in which the barrier sheet 1070 is coiled. Delivery may, therefore be accomplished by pushing or ejecting the barrier sheet 1070 and allowing it to uncoil within the submucosal space 1002.

Figure 52:
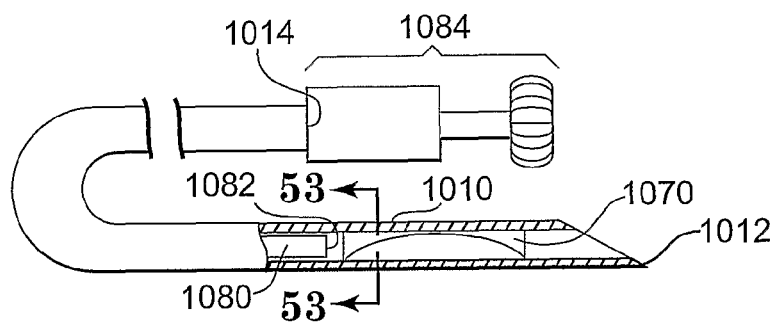
FIG. 52 is a partial cross-sectional view of an apparatus that may be used to deliver a barrier sheet.

The coiled barrier sheet 1070 may preferably be located proximate a distal end 1012 of a delivery sheath 1010 as depicted in, e.g., FIG. 52. As a result, the barrier sheet 1070 is preferably located within a lumen 1020 of the delivery sheath 1010 when inserting the barrier sheet 1070 into the submucosal space 1002. During deployment of the barrier sheet 1070, it may be moved out of the lumen 1020 of the sheath 1010 through an opening at the distal end of the delivery sheath 1010. Because the barrier sheet 1070 is restrained in its coiled configuration while in the lumen 1020, ejecting the barrier sheet 1070 from the lumen 1020 results in uncoiling the barrier sheet 1070 within the submucosal space 1002.

Although many different techniques may be used to move the barrier sheet 1070 out of the lumen 1020, one exemplary method depicted in FIG. 52 includes an ejection device 1080 that may preferably advance toward the distal end 1012, forcing the barrier sheet 1070 out of the lumen 1020 using surface 1082 as it advances distally (i.e., in the distal direction of the sheath 1010). The ejection device 1080 may preferably be operably connected to an actuator 1084 that may preferably be located proximate the proximal end 1014 of the delivery sheath 1010.

Another optional feature depicted in FIG. 52 is that the distal end 1012 of the sheath 1010 may preferably be adapted to pierce or perforate tissue, such as the tissue of a bleb, such that the opening of the lumen 1020 is located within the submucosal space where the barrier sheet 1070 can be deployed. Alternatively, the sheath 1010 may be inserted into the submucosal space through a variety of other techniques and/or apparatus.

It should be understood that the depicted sheath, ejection device, actuator, etc. depicted in FIG. 52 are exemplary in nature only and that any suitable apparatus or mechanism that can deliver and deploy the barrier sheets of the present invention may be used.

Figure 53:
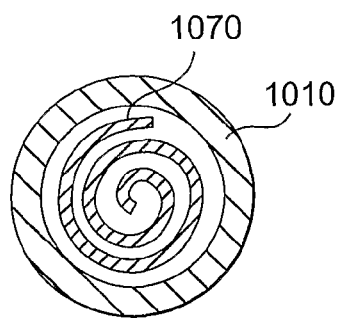
FIG. 53 is a cross-sectional view of the apparatus of FIG. 52 taken along line 53-53 in FIG. 52.
Figure 54:
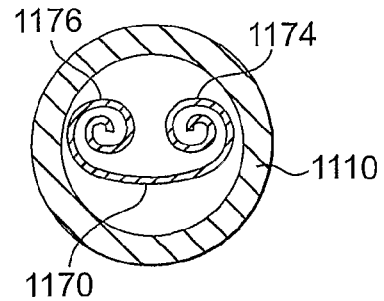
FIG. 54 is a cross-sectional view of an alternative barrier sheet within the lumen of a delivery sheath.

Another variation in connection with the barrier sheets of the present invention may be depicted in FIGS. 53 & 54. In particular, FIG. 53 is a cross-sectional view of barrier sheet 1070 and sheath 1010 taken along line 53-53 in FIG. 52. The barrier sheet 1070 includes only one coil when located within lumen 1020. Alternatively, the barrier sheets of the present invention may be stored within the lumen of delivery sheath in a variety of other configurations. One such alternative is depicted in the cross-sectional vie of FIG. 54 in which barrier sheet 1170 includes two coils 1174 & 1176 when located within lumen 1120 of sheath 1110. The coils 1174 & 1176 may preferably be rolled inwardly towards each other in opposing directions as depicted. A potential advantage of a two-coil configuration is that uncoiling of the barrier sheet 1170 within a submucosal space may be facilitated with two smaller coils such as are depicted in FIG. 54.

The barrier sheets of the present invention may be manufactured of a variety of different materials, although the materials may preferably possess the functional characteristics discussed herein (such as, e.g., flexibility and memory sufficient to allow for coiling and uncoiling). In some embodiments, the barrier sheets may preferably be constructed of biosorbable materials. Some exemplary materials may include, e.g., films, woven fabrics, non-woven fabrics, laminates of films and/or fabrics, etc. The materials may include, e.g., GORE-TEX fabrics, polypropylene, polyurethane, etc. It may be preferred that the materials used to construct the barrier sheets resist electro-cautery currents (e.g., possess low electrical conductivity). Examples of some suitable materials may be described in, e.g., U.S. Patent Application Publication No. US 2002/0161114 A1 (Gunatillake et al.),U.S. Pat. No. 6,080,474 (Oakley et al.), U.S. Pat. No. 6,021,524 (Wu et al.), and U.S. Pat. No. 5,368,930 (Samples).

The thickness of the materials used for barrier sheets of the present invention may preferably be, e.g., 1 millimeter or less (although in some instances, the thickness may be greater, e.g., for use in laparoscopic procedures). The overall size of the barrier sheets may also be dependent on the needs of a selected procedure, e.g., in some instances, the barrier sheets may be 10 centimeters or more across and in other procedures, the barrier sheets may be 1 centimeter or less across.

Figure 55:
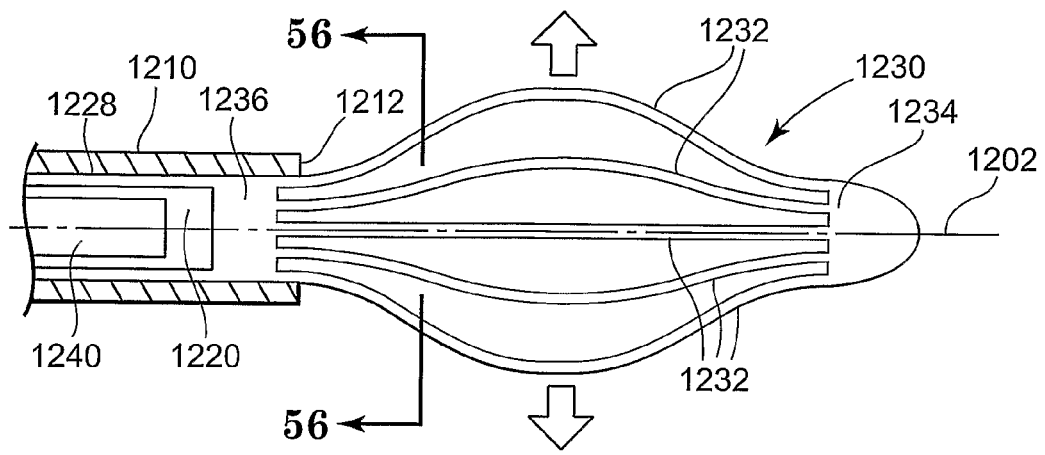
FIG. 55 is a partial cross-sectional view of a portion of an expandable cage delivery apparatus.
Figure 56:
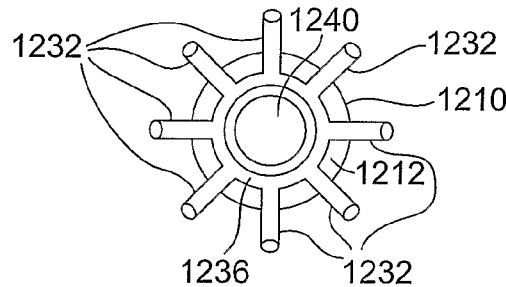
FIG. 56 is a cross-sectional view of the apparatus of FIG. 55 taken along line 56-56 in FIG. 55.

Still another apparatus that may be used to assist in tissue resection is depicted in FIGS. 55 & 56. The depicted apparatus may be used to prop open a variety of internal body locations, such as, e.g., body lumens (colon, gastro-intestinal, blood vessels, urinary tract, etc.). In connection with blebs, the apparatus of FIGS. 55 & 56 may be used to maintain the submucosal space in the absence of, e.g., the gas, liquid, or other material used to create the submucosal space.

The depicted device includes a delivery sheath 1210 and a cage 1230. The delivery sheath 1210 includes a lumen with an opening at a distal end of the delivery sheath 1210. The delivery sheath 1210 defines a longitudinal axis extending between its distal end and a proximal end. The cage 1230 is operatively connected to an actuator that extends through the lumen to the proximal end of the delivery sheath 1210. The actuator is preferably movable to advance the cage 1230 out of the lumen and retract the cage 1230 within the lumen. The cage 1230 can be advanced out of the lumen 1220 of the sheath 1210 such that the cage 1230 expands to, e.g., support tissue.

The cage 1230 includes struts 1232 that extend between a distal retainer 1234 and a proximal retainer 1236. The proximal retainer 1236 may preferably be operated from a proximal end of the apparatus such that the sheath 1210 and the cage 1230 can be moved relative to each other in the proximal and distal directions. Movement such that the cage 1230 extends out of the lumen 1220 of the sheath 1210 may be accomplished using an actuator 1228 (the distal end of which is depicted in FIG. 55).

The struts 1232 of the cage 1230 may preferably be in a restrained configuration when located within the lumen 1220 and an expanded configuration when advanced distally out of the lumen 1220. In the expanded configuration as depicted in FIG. 55, the struts 1232 preferably move radially outward from the longitudinal axis 1202 that extends along the length of the sheath 1210. The struts 1232, when deployed outside of the lumen 1220 may not fully expand if they are in an internal body location that constrains their expansion. The force applied by the struts 1232 on the surrounding tissue may, however, preferably force the tissue outward from the longitudinal axis 1202.

Although the struts 1232 are depicted as expanding generally equally in all directions, it will be understood that they may preferentially expand on only one or more directions. In addition, although the struts 1232 are depicted as taking a generally bell-shape when expanded, it will be understood that they may take a variety of different shapes.

The expansion force used to expand the cage 1230 may preferably be supplied by the struts 1232 themselves which may preferably be constructed of materials that can be restrained within the lumen 1220 of sheath 1210 for delivery, but can then expand when released from the constraints of the lumen 1220. It may further be preferred that the struts 1232 possess physical characteristics such as elasticity and resiliency that allow the cage 1230 to be retracted back into lumen 1220 after advancement out of the lumen 1220. Retraction and advancement may preferably be used to control the size of the cage 1230 within, e.g., the submucosal space of a bleb or any other selected location (e.g., internal body lumens in the colon, gastro-intestinal system, blood vessels, urinary tract, etc.).

Examples of suitable materials for the struts 1232 of the cage 1230 may include, e.g., metals, polymers, shape memory metals, shape memory polymers, etc. The distal and proximal retainers 1234 and 1236 may be made of the same or different materials.

Another optional feature of the apparatus depicted in FIGS. 55 & 56 is that the cage 1230 may be designed to allow the passage of an apparatus 1240 into the volume of the expanded cage 1230. The apparatus 1240 may be, e.g. an imaging device (e.g., colonoscope, etc.), resection device (for resecting tissue surrounding or extending into the cage 1230), etc. The apparatus 1240 may preferably be movable longitudinally within the delivery sheath 1210, wherein the device 1240 can be advanced into the cage 1230 when the cage 1230 is in the expanded configuration. It may also be preferred that the apparatus 1240 be capable of retraction in the proximal direction such that the apparatus 1240 can be withdrawn back into the delivery sheath 1210.

Although only one lumen is depicted in delivery sheath 1210, it should be understood that multiple lumens could be provided to allow for independent advancement and retraction of the cage 1230 and apparatus 1240. Further, although only one apparatus 1240 is depicted, it should be understood that more than one apparatus could be advanced into the cage 1230 at one time.

Figure 57:
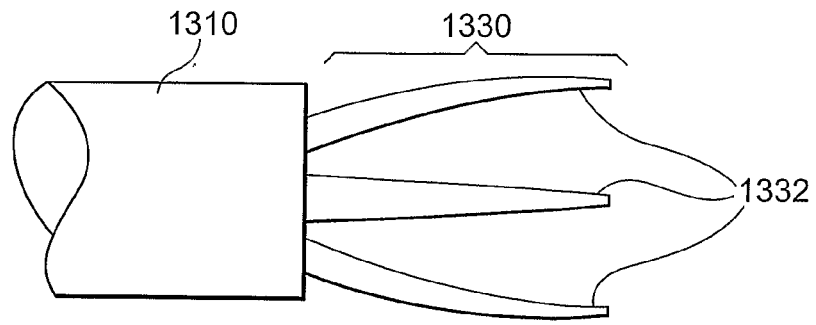
FIG. 57 is a view of an alternative expandable cage device.

Still another variation of the apparatus is depicted in FIG. 57 in which a cage 1330 is provided without a distal retainer such that as the sheath 1310 is withdrawn, the struts 1332 of the cage 1330 expand in the absence of distal retainer. Although a distal retainer such as that seen in FIG. 55 is not included, the distal ends of the struts 1332 may still be connected to each other if so desired. Advancement of the sheath 1310 in the distal direction may preferably cause the cage 1320 to collapse such that the struts 1332 are again contained within the sheath 1310 (as described above in connection with, e.g., the embodiment of FIGS. 55 & 56).

Although not depicted, the apparatus of the present invention may use a variety of different actuating mechanisms to move the needles, resection frames, staples, jaws, cutting members, snares, etc. The actuators may be in the form of electromagnetic actuators, hydraulic actuators, pneumatic actuators, screw drives, push/pull rods extending the length of the elongated body for manual operation by a user, etc. Typically, the specific actuating mechanism(s) selected will be known to those of skill in the art of medical devices. In addition, the resection devices of the invention may preferably be mounted on elongated bodies for delivery to internal body locations, potentially through or on an endoscope. The materials used to construct the various resection devices may preferably be those materials suitable for use in medical devices, e.g., metals, polymers, composite materials, etc.

As used herein and in the appended claims, the singular forms "a," "and," and "the" include plural referents unless explicitly limited to the singular form or the context clearly dictates otherwise.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. An endoscopic resection apparatus comprising:
an elongated body comprising a proximal end and a distal end;
a resection frame located proximate the distal end of the elongated body, the resection frame comprising two spaced apart rails and a cross member, wherein the resection frame comprises an extended position and a retracted position, and wherein the two spaced apart rails and the cross member of the resection frame define a resection plane between the rails and the cross member;
a cutting instrument located on the cross member between the two spaced apart rails of the resection frame, wherein the cutting instrument is displaced from the distal end of the elongated body when the resection frame is in the extended position, and wherein movement of the resection frame to the retracted position moves the cutting instrument towards the distal end of the elongated body moves the cutting instrument within the resection plane;
wherein the cross member comprises either a plurality of staples or a stapling anvil, and wherein the plurality of staples and the stapling anvil are located on opposite sides of the resection opening when the resection frame is in the extended position, and further wherein movement of the resection frame into the retracted position moves the plurality of staples or the stapling anvil on the cross member within the resection plane and forces the plurality of staples into contact with the stapling anvil; and
a resection opening defined by the two spaced apart rails and the cutting instrument when the resection frame is in the extended position, wherein the size of the resection opening decreases and wherein tissue extending through the resection opening is severed by the cutting instrument when the resection frame is moved into the retracted position from the extended position.

2. An apparatus according to claim 1, wherein the cutting instrument comprises a blade.

3. An apparatus according to claim 1, wherein the two spaced apart rails comprise rigid members.

4. An apparatus according to claim 1, wherein the two spaced apart rails and the cutting instrument of the resection frame define a U-shaped resection opening.

5. An apparatus according to claim 1, further comprising a fluid delivery lumen extending through at least a portion of the elongated body, the fluid delivery lumen terminating proximate the distal end of the elongated body, the apparatus further comprising a needle attached to the fluid delivery lumen proximate the distal end of the elongated body, wherein the needle is movable between an injection position in which the needle extends from the distal end of the elongated body and a sheathed position in which the needle is located within the elongated body.

6. An apparatus according to claim 5, further comprising a fluid source connected to the fluid delivery lumen, the fluid source comprising a fluid adapted to form submucosal fluid cushions in mucosal tissue.

7. An apparatus according to claim 6, wherein the fluid comprises a liquid.

8. An apparatus according to claim 6, wherein the fluid comprises a gas.

9. An apparatus according to claim 1, wherein the plurality of staples and the stapling anvil staple tissue extending through the resection opening when the resection frame is moved into the retracted position from the extended position.

* * * * *